United States Patent
Salzman

(10) Patent No.: US 11,028,440 B2
(45) Date of Patent: *Jun. 8, 2021

(54) METHODS FOR IDENTIFYING AND USING SMALL RNA PREDICTORS

(71) Applicant: SRNALYTICS, INC., Needham, MA (US)

(72) Inventor: David Salzman, Needham, MA (US)

(73) Assignee: GATEHOUSE BIO, INC., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/029,036

(22) Filed: Jul. 6, 2018

(65) Prior Publication Data
US 2018/0305763 A1     Oct. 25, 2018

Related U.S. Application Data

(63) Continuation of application No. 15/877,989, filed on Jan. 23, 2018.

(60) Provisional application No. 62/449,275, filed on Jan. 23, 2017.

(51) Int. Cl.
    *C12Q 1/6883*        (2018.01)

(52) U.S. Cl.
    CPC ..... *C12Q 1/6883* (2013.01); *C12Q 2600/158* (2013.01); *C12Q 2600/178* (2013.01)

(58) Field of Classification Search
    CPC ............ C12Q 1/6883; C12Q 2600/158; C12Q 2600/178
See application file for complete search history.

(56) References Cited

U.S. PATENT DOCUMENTS

| | | | |
|---|---|---|---|
| 9,683,264 | B2 | 6/2017 | Burwinkel et al. |
| 2006/0263798 | A1 | 11/2006 | Huynh et al. |
| 2012/0088687 | A1 | 4/2012 | Goel et al. |
| 2015/0315659 | A1 | 11/2015 | Burwinkel et al. |
| 2019/0249262 | A1 | 8/2019 | Rigoutsos et al. |

FOREIGN PATENT DOCUMENTS

| | | |
|---|---|---|
| WO | 2008153692 | 12/2008 |
| WO | 2011163214 | 4/2011 |
| WO | 2013036936 | 3/2013 |
| WO | 2014179765 | 11/2014 |
| WO | 2015081229 | 6/2015 |
| WO | 2018076015 A1 | 4/2018 |
| WO | 2019094780 | 5/2019 |

OTHER PUBLICATIONS

Hoss, A.G. et al., miR-10b-5p expression in Huntington's disease brain relates to age of onset and the extent of striatal involvment, BMC Med. Genomics, vol. 8:10, pp. 1-14 (Year: 2015).*

Grasso, M. et al., Circulating miRNAs as Biomarkers for Neurodegenerative Disorders, Molecules, vol. 19, pp. 6891-6910 (Year: 2014).*

Marti, E. et al., A myriad of miRNA variants in control and Huntington's disease brain regions detected by massively parallel sequencing, Nucl. Acids Res., vol. 38, pp. 7219-7235 (Year: 2010).*

Diez-Planelles, C. et al., Circulating microRNAs in Huntington's disease: Emerging mediators in metabolic impairment, Pharmacol. Res., vol. 108, pp. 102-110 (Year: 2016).*

Reed, E.R. et al., MicroRNAs in CSF as prodromal biomarkers for Huntington disease in the PREDICT-HD study, Neurology, vol. 90:e 1-9 (Year: 2018).*

Raabe, C.A. et al., Biases in small RNA deep sequencing data, Nucl. Acids Res., vol. 42, pp. 1414-1426 (Year: 2014).*

Bachmann, L.M. et al., Sample sizes of studies on diagnostic accuracy: literature survey, BMJ, vol. 332, pp. 1127-1129 (Year: 2006).*

MiRBase database (http://mirbase.org/cgibin/mirna_summary.pl?org=hsa; accessed Mar. 21, 2019) (Year: 2019).*

Dard-Dascot, C. et al., Systematic comparison of small RNA library preparation protocols for next-generation sequencing, BMC Genomics, vol. 19:118, pp. 1-16 (Year: 2018).*

Dard-Dascot, C. et al., Systematic comparison of small RNA library preparation protocols for next-generation sequencing, BMC Genomics, vol. 19:118, Supplemental material S1, S2 and S8-S10 (Year: 2018).*

Roberts, B.S. et al., Blocking of targeted microRNAs from next-generation sequencing libraries, NAR, vol. 43, e145, pp. 1-8 (Year: 2015).*

Schwarzenbach, H. et al., Data Normalization Strategies for MicroRNA QuantificationClin. Chem., vol. 61, pp. 1333-1342 (Year: 2015).*

Serafin, A. et al., Identification of a set of endogenous reference genes for miRNA expression studies in Parkinson's disease blood samples, BMC Res. Notes, vol. 7:715, pp. 1-9 (Year: 2014).*

(Continued)

*Primary Examiner* — Teresa E Strzelecka
(74) *Attorney, Agent, or Firm* — Morgan, Lewis & Bockius LLP

(57) ABSTRACT

The invention provides a method for identifying or detecting small RNA (sRNA) predictors of a disease or a condition. The method comprises identifying one or more sRNA sequences that are present in one or more samples of an experimental cohort, and which are not present across a comparator cohort; and optionally identifying one or more sRNA sequences that are present in one or more samples of a comparator cohort, and which are not present across an experimental cohort. In contrast to identifying dysregulated non-coding RNAs (such as miRs that are up- or down-regulated), the invention identifies sRNAs that are binary predictors, that is, present in one cohort (e.g., an experimental cohort) and not another (e.g., a comparator cohort). Further, by quantifying reads for individual sequences (e.g., iso-miRs), without consolidating reads to annotated reference sequences, the invention unlocks the diagnostic utility of miRs and other sRNAs.

22 Claims, 13 Drawing Sheets

Specification includes a Sequence Listing.

(56) References Cited

OTHER PUBLICATIONS

SRNA-FIND, sRNAlytics (https://www.srnalytics.com/use-cases-of-technology, downloaded on Mar. 20, 2019 (Year: 2019).*
FDA Letter of Support to Dr. Salzman dated Jan. 17, 2019, pp. 1-2 (Year: 2019).*
PiRBase, donloaded from http://regulatoryrna.org/database/piRNA/browse.php on Mar. 21, 2019 (Year: 2019).*
Bossyut, P. M.M., Clinical validity: Defining biomarker performance, Scand. J. Clin. & Lab. Invest., vol. 70, suppl. 242, pp. 46-52 (Year: 2010).*
Koppers-Lalic et al., Nontemplated Nucleotide Additions Distinguish the Small RNA Composition in Cells from Exosomes, Cell Reports 8: 1649-1658 (2014).
International Search Report, for International Application No. PCT/US2018/014856, dated Jun. 28, 2018, 11 pages.
Ioannidis, J.P.A. et al., Comparison of Effect Sizes Associated With Biomarkers Reported in Highly Cited Individual Articles and in Subsequent Meta-analyses, JAMA, vol. 305, pp. 2200-2210 (Year: 2011).
Wenjing Kang et al.: "Computational Prediction of miRNA Genes from Small RNA Sequencing Data", Frontiers in Bioengineering and Biotechnology, vol. 3, Jan. 26, 2015 (Jan. 26, 2015), XP055735894.
Muserref Duygu Sacar et al., "Can MiRBase Provide Positive Data for Machine Learning for the Detection of Mi RNA Hairpins?", Journal of Integrative Bioinformatics, Jan. 1, 2013, pp. 1-11, XP055735739.
William Ritchie et al.,: "Defining and providing robust controls for microRNA prediction", Bioinformatics, vol. 28, No. 8, Apr. 15, 2012, pp. 1058-1061, XP055735743.
Marcel Martin: "Cutadapt removes adapter sequences from high-throughput sequencing reads", EMBNET. Journal, vol. 17, Aug. 2, 2011, p. 10, XP055737194.
MiRBase database, human sequences, downloaded from www.mirbase.org/textsearch.shtml?q=human&submit=submit; dowloaded May 28, 2020 (Year: 20).
PiRBase database, human sequences, downloaded from http://regulatoryrna.org/database/piRNA/browse.php on May 28, 2020 (Year: 2020).
Farazi, T.A. et al., Micro RNA Sequence and Expression Analysis in Breast Tumors by Deep Sequencing, Cancer Res., vol. 71, pp. 4443-4453 (Year: 2011).
Telonis, A.G. et al., Beyond the one-locus-one-mi RNA paradigm: microRNA isoforms enable deeper insights into breast cancer heterogeneity, Nucl. Acids Res., vol. 43, pp. 9158-9173 (Year: 2015).

* cited by examiner

FIGURE 1A
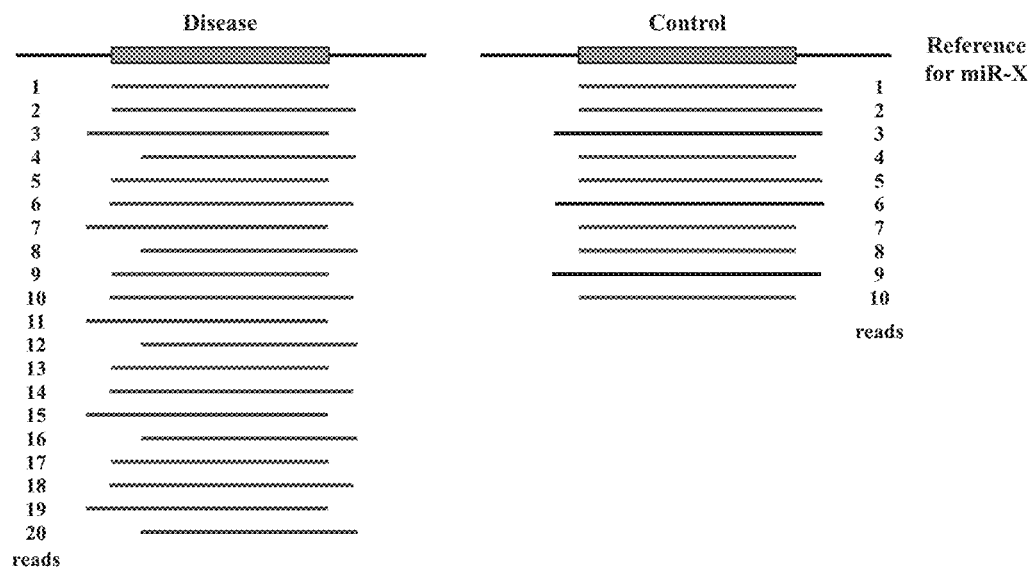
FIGURE 1B
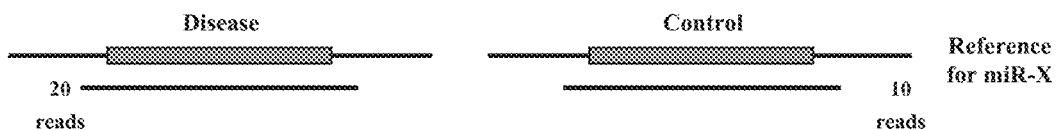
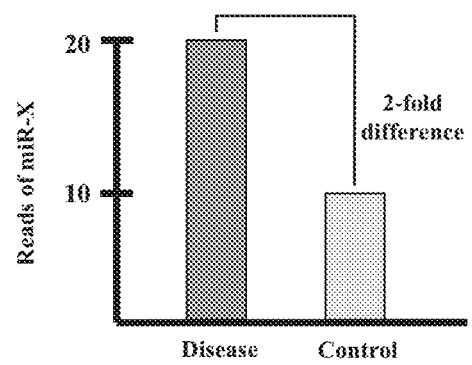

FIGURE 2

| | | Huntington's Disease SRR1759249 | Healthy Control SRR1759213 | |
|---|---|---|---|---|
| | miR-10b sequence (5' - 3') | Number of reads | Number of reads | |
| (SEQ ID NO:2) | ATATACCCTGTAGAACCGAATTTGTGTGG | | | Reference |
| (SEQ ID NO:3) | TACCCTGTAGAACCGAATTTGTG | 925 | 196 | Annotated miR-10b |
| (SEQ ID NO:4) | TACCCTGTAGAACCGAATTTGTGA | 213 | 33 | miR-10b iso-miR 1 |
| (SEQ ID NO:5) | ACCCTGTAGAACCGAATTTGTG | 203 | 51 | miR-10b iso-miR 2 |
| (SEQ ID NO:6) | ACCCTGTAGAACCGAATTTGTGT | 138 | 25 | miR-10b iso-miR 3 |
| (SEQ ID NO:7) | ACCCTGTAGAACCGAATTTGTGA | 107 | 27 | miR-10b iso-miR 4 |
| (SEQ ID NO:8) | TACCCTGTAGAACCGAATTTGTGG | 36 | 3 | miR-10b iso-miR 5 |
| (SEQ ID NO:9) | ACCCTGTAGAACCGAATTTGTGG | 31 | 1 | miR-10b iso-miR 6 |
| (SEQ ID NO:10) | TACCCTGTAGAACCGAATTTGTGAA | 10 | 0 | miR-10b iso-miR 7 |
| (SEQ ID NO:11) | ACCCTGTAGAACCGAATTTGTGAA | 7 | 0 | miR-10b iso-miR 8 |
| | Total Read Count | 1670 | 336 | |
| | Fold Difference | 5-fold more miR-10b in Huntington's Disease sample (SRR1759249) compared to Healthy Control (SRR1759213) | | |

FIGURE 5

|  | | TaqMan Assay | | |  |
|---|---|---|---|---|---|
|  | | Annotated miR | iso-miR 1 | iso-miR 2 |  |
| Synthetic RNA | Annotated miR | 100.0 | 0.0 | 0.0 | Relative Detection (%) |
| | iso-miR 1 | 0.0 | 100.0 | 0.0 | |
| | iso-miR 2 | 0.0 | 0.0 | 100.0 | |

```
Annotated miR: UGAGAACUGAAUUCCAUGGGUU     SEQ ID NO: 12
   iso-miR 1:  UGAGAACUGAAUUCCAUGGGUUU    SEQ ID NO: 13
   iso-miR 2:  UGAGAACUGAAUUCCAUGGGUUG    SEQ ID NO: 14
```

METHODS FOR IDENTIFYING AND USING SMALL RNA PREDICTORS

PRIORITY

This application claims the benefit of, and priority to, U.S. Provisional Application No. 62/449,275, filed Jan. 23, 2017, the contents of which are hereby incorporated by reference in its entirety.

BACKGROUND microRNAs (abbreviated miRNAs or miRs) are small non-coding RNA molecules (about 22 nucleotides in length) found in plants and animals that function in RNA silencing and post-transcriptional regulation of gene expression. miRNAs are located within the cell, as well as in the circulation and extracellular environment, and can be detected in biological fluids.

An analysis of miRNAs highly conserved in vertebrates shows that each has roughly 400 conserved messenger RNA (mRNA) targets. Accordingly, a particular miRNA can reduce the stability of hundreds of unique mRNAs, and may repress the production of hundreds of proteins. This repression is often relatively mild, for example, usually less than 2-fold. Human disease can be associated with deregulation or dysregulation of miRNAs as demonstrated for chronic lymphocytic leukemia and other B cell malignancies. A manually curated, publicly available database, miR2Disease, documents known relationships between miRNA levels (up- or down-regulated miRNAs) and human disease.

However, despite the clear role that miRNAs and other small non-coding RNAs have in the biology of cells and their association with human disease, their diagnostic potential has not been realized. It is an objective of the present invention to unlock the diagnostic potential of miRNAs and other small, non-coding RNAs (sRNAs).

SUMMARY OF THE INVENTION

In various aspects and embodiments, the invention provides a method for identifying or detecting small RNA (sRNA) predictors of a disease or a condition. The method comprises identifying one or more sRNA sequences that are present in one or more samples of an experimental sample cohort, and which are not present in samples of a comparator cohort ("positive sRNA predictor"). In some embodiments, the method further comprises identifying one or more sRNA sequences that are present in one or more samples of a comparator sample cohort, and which are not present in samples of an experimental cohort ("negative sRNA predictor"). In contrast to identifying dysregulated small RNAs (such as microRNAs (miRNAs or miRs) that are up- or down-regulated), the invention identifies sRNAs that are binary predictors, that is, present in one cohort (e.g., an experimental cohort) and not another (e.g., a comparator cohort). Further, by quantifying reads for individual sequences (e.g., iso-miRs), without consolidating reads to annotated reference sequences, the invention unlocks the diagnostic utility of miRs and other sRNAs. In some embodiments, the one or more sRNA predictors, or a set of sRNA predictors, is validated in an independent cohort of experimental and comparator samples, different from the experimental and comparator samples from whence they were discovered, to evaluate the ability of the sRNA predictors to discriminate experimental and comparator samples.

In various embodiments, sRNA predictors are identified from sRNA sequencing data. Specifically, sRNA sequencing data is generated or provided for samples across an experimental cohort and a comparator cohort, for example, using any next-generation sequencing platform. sRNA predictors can be identified in sequence data from any type of biological sample, including solid tissues, biological fluids (e.g., cerebrospinal fluid and blood), or in some embodiments, cultured cells. The invention is applicable to various types of eukaryotic and prokaryotic cells and organisms, including animals, plants, and microbes.

Generally, sRNA predictors can be identified for various utilities in understanding the state of cells or organisms, including utilities in human and animal health, as well as agriculture. For example, the invention finds use in diagnostics, prognostics, drug discovery, toxicology, and therapeutics including personalized medicine. In some embodiments, the invention provides for diagnosis or stratification of a human or animal disease. For example, conditions that can define the experimental cohort include neurodegenerative diseases, cardiovascular diseases, inflammatory and/or immunological diseases, and cancers. Further, sRNA predictors can be identified for detecting a disease state, including early or asymptomatic stage disease (e.g., before noticeable or substantial symptoms appear) or distinguishing among diseases or conditions that manifest with similar symptoms. Exemplary conditions include diagnosis (including early diagnosis) or stratification of neurodegenerative conditions such as Alzheimer's Disease, Parkinson's Disease, Huntington's Disease, Amyotrophic Lateral Sclerosis, and Multiple Sclerosis.

The sRNA predictor(s) may be identified by a software program that quantifies the number of reads for each unique sRNA sequence in each sample in the experimental and comparator cohorts. In various embodiments, the software program trims the adaptor sequences from the individual sequences, so as to identify individual sRNAs, including miRs and iso-miRs. In this manner, iso-miRs with templated and non-templated variations at the 3'- and 5'-end are identified, among other sRNAs. After trimming, the sequence reads from the experimental cohort and the comparator cohort can each be compiled into a dictionary, and compared, to identify sequences that are present in one cohort, but not the other. Unique sequences and the amount (i.e. read count) of the unique reads for each sample or group of samples in the experimental cohort are annotated. sRNA sequences are not aligned to a reference sequence, and thus, each sequence can be individually quantified across samples.

In some embodiments, sRNA predictors are selected that have a read count of at least 5 or at least about 50 in the samples from the experimental cohort that are positive for the sRNA predictor. In still other embodiments, the sRNA predictors are present in at least about 7% of the experimental cohort samples, or are present in at least about 10/o of comparator samples. In some embodiments, several sRNA predictors (such as four or more) are identified in the experimental cohort and/or the comparator cohort, and which may be selected for inclusion in an sRNA predictor panel. For example, binary predictors identified in the experimental cohort are positive predictors, while binary predictors identified in the comparator cohort are negative predictors.

In some embodiments, a panel of sRNA predictors is selected for validation or detection of the condition in independent samples. For example, a panel of from 1 to about 200, or from 1 to about 100, or from 1 to about 50 sRNA, or from 1 to about 10 predictors can be selected, where the presence of one or more positive predictors (optionally with the absence of one or more negative predictors) is predictive of the condition that defines the experimental cohort. In some embodiments, the presence of 1, 2, 3, 4, 5, 6, 7, 8, 9 or 10 positive predictors from the panel, optionally with an absence of the entire panel of negative predictors, is predictive of the condition. While not each experimental sample will be positive for each positive predictor, the panel is large enough to provide nearly complete coverage for the condition in the experimental cohort or in independent samples (e.g., the population). For example, the presence of from 1 to about 100, or from 1 to about 50, or from 1 to about 20, or from 1 to about 10 sRNA positive predictors in a sample can be predictive of the condition that defines the experimental cohort. Validation samples can be evaluated by sRNA sequencing, or alternatively by RT-PCR (including Real Time PCR or any quantitative or qualitative PCR format) or other sRNA detection assay.

In various embodiments, detection of the sRNA predictors is migrated to one of various detection platforms, which can employ reverse-transcription and amplification, and/or hybridization of a detectable probe (e.g., fluorescent probe). An exemplary format is TAQMAN RealTime PCR Assay. Alternatively, sRNA predictors in the panel, or their amplicons, are detected by a hybridization assay.

In other aspects, the invention provides a kit comprising a panel of from 1 to about 200 or from 1 to about 100, or from 1 to 50 sRNA predictor assays, which may include one or both of positive and negative predictors. Such assays may comprise amplification primers and/or probes specific for the detection of the sRNA predictors over annotated sequences, as well as over other (non-predictive) 5'- and/or 3'-templated and/or non-templated variations. In some embodiments, the kit is in the form of an array, and may contain probes specific for the detection of sRNA predictors by hybridization. The majority, or all, of the sRNA predictors are sRNAs in which any miRNA predictors contain a variation from a reference miRNA sequence.

In other aspects, the invention provides a method for determining a condition of a subject. The method comprises obtaining a biological fluid sample, and identifying the presence or absence of one or more sRNA predictors identified in RNA sequence data according to the methods described herein, where the presence of one or more positive sRNA predictors in the sample, and optionally the absence of one or more negative predictors, is predictive or diagnostic for the condition. In some embodiments, the sRNA predictor(s) are identified in a sample from a human patient by a detection technology that involves amplification and/or probe hybridization, such as Real Time PCR (e.g., TAQMAN) assay. The biological fluid sample from the patient can be blood, serum, plasma, urine, saliva, or cerebrospinal fluid.

In various embodiments, the patient is suspected of having a neurodegenerative disease, a cardiovascular disease, an inflammatory and/or immunological disease, or a cancer. For example, the patient may be displaying one or more symptoms of the condition. In some embodiments, the patient is suspected of having a neurodegenerative disease selected from Amyotrophic Lateral Sclerosis (ALS), Parkinson's Disease, Alzheimer's Disease, Huntington's Disease, or Multiple Sclerosis.

The sample is tested across a panel of sRNA detection assays, such as from 1 to about 100, or from about 4 to 100 sRNA detection assays, and in some embodiments the majority of the sRNAs detected in the patient sample (or all of the sRNAs detected in the patient sample) are not annotated reference miRNAs. The panel may however include one or more miRNAs for detection as a control.

In other aspects of the invention, positive and/or negative predictors can be employed to classify a mixed population of cells in vivo or ex vivo, through targeted expression of a gene with a detectable or biological impact. For example, a desired protein can be expressed from a gene construct (such as a plasmid) or expressed from mRNA delivered to cells in vivo or ex vivo. In these embodiments, the gene is delivered under the regulatory control of target site(s) specific for the one or more small RNA predictors. The target site(s) (target sites for specific hybridization with the predictors) can be placed in non-coding segments, such as the 3' and/or 5' UTRs, such that the encoded protein is only expressed in biologically significant amounts when the desired predictor(s) are absent in the cell. The protein encoded by the construct may be a reporter protein, a transcriptional activator, a transcriptional repressor, a pro-apoptotic protein, a pro-survival protein, a lytic protein, an enzyme, a cytokine, a toxin, or a cell-surface receptor. In these aspects, the predictors can be used to target expression of a desired protein for therapeutic impact, either to target diseased cells for killing, or to protect non-diseased cells from toxic insult.

Other aspects and embodiments of the invention will be apparent from the following examples.

DESCRIPTION OF THE FIGURES

FIGS. 1A and 1B illustrates the standard method for analyzing small RNA sequencing data, from embodiments of the present invention. The object of standard processes is to identify dysregulated sRNAs (up- or down-regulated) for validation in larger cohorts using targeted assays such as quantitative PCR (e.g., TAQMAN). For sequence analysis, adapter sequences are trimmed, reads are aligned to a reference, and read numbers are quantified for each reference sRNA. Diagnostic sRNAs are selected based on the level of differential expression between samples and/or groups of samples. FIG. 1A is an illustrative example showing mapped small RNA sequence reads (in this case a miRNA, miR-X) aligned to a reference. As shown, miR-X is present in both a Disease and Control sample, and is not a homogenous sequence, but rather a heterogeneous series of iso-miRs that all map to the same region. Lines representing sequence reads are shaded to depict various iso-miR sequences. The light grey box highlights the annotated miR-X reference sequence. FIG. 1B is an illustrative example of how the mapped sequencing data for miR-X from FIG. 1A is condensed and quantified, which is the sum of all of the iso-miRs for miR-X. In this particular example, miR-X would be considered to have diagnostic value/potential, since there is a 2-fold difference in expression when comparing the Disease and Control sample.

FIG. 2 illustrates sequencing data for the human miRNA, miR-10b derived from a frontal cortex (region BA9) tissue sample taken from a patient with Huntington's Disease (SRR1759249) or non-diseased, Healthy Control (SRR1759213). The reference is shown with the annotated miR-10b sequence highlighted. The number of reads for each sequence is shown. In this particular example, there are 8 miR-10b iso-miRs in addition to the annotated miR-10b sequence found in these samples. The total read count for the Huntington's Disease and Healthy Control samples are 1670 and 336, respectively. Thus, there is 5-fold greater amount of 'total' miR-10b in the Huntington's Disease sample when compared to the Healthy Control.

FIG. 3A illustrates the approach according to the present disclosure, where iso-miRs (or other sRNAs) are sorted by their individual iso-miR sequences, and therefore do not require alignment to a reference. Lines representing sequence reads are shaded to depict identical iso-miR sequences. FIG. 3B shows how sequence reads for iso-miRs (or other sRNAs) are quantified based on their unique sequence, not by alignment to a reference.

FIG. 4 illustrates that the miR-X annotated sequence is present in equal amounts in both the Disease and Control sample, and is therefore non-diagnostic. Additionally, FIG. 4 illustrates that a miR-X iso-miR is present in both the Disease and Control sample with a 2.5-fold difference, however since this iso-miR is not binary, it is not included in a diagnostic panel.

FIG. 5 illustrates that quantitative PCR assays (e.g., based on TAQMAN format) can be designed that give >99.9% specificity for iso-miRs or other sRNAs of interest. Here, hairpin-RT TAQMAN qPCR assays were designed for the indicated annotated miR, iso-miR 1 (that has an additional 3'-terminal uridine) or iso-miR 2 (that has an additional 3'-terminal guanidine). Synthetic RNA, as indicated was reverse transcribed using a targeted hairpin-RT primer. cDNA was amplified by qPCR in the presence of a TAQMAN probe specific to each RNA sequence. Shown is the percent relative detection, for a TAQMAN assay to detect each synthetic RNA.

DETAILED DESCRIPTION OF THE INVENTION

Figure 3A:
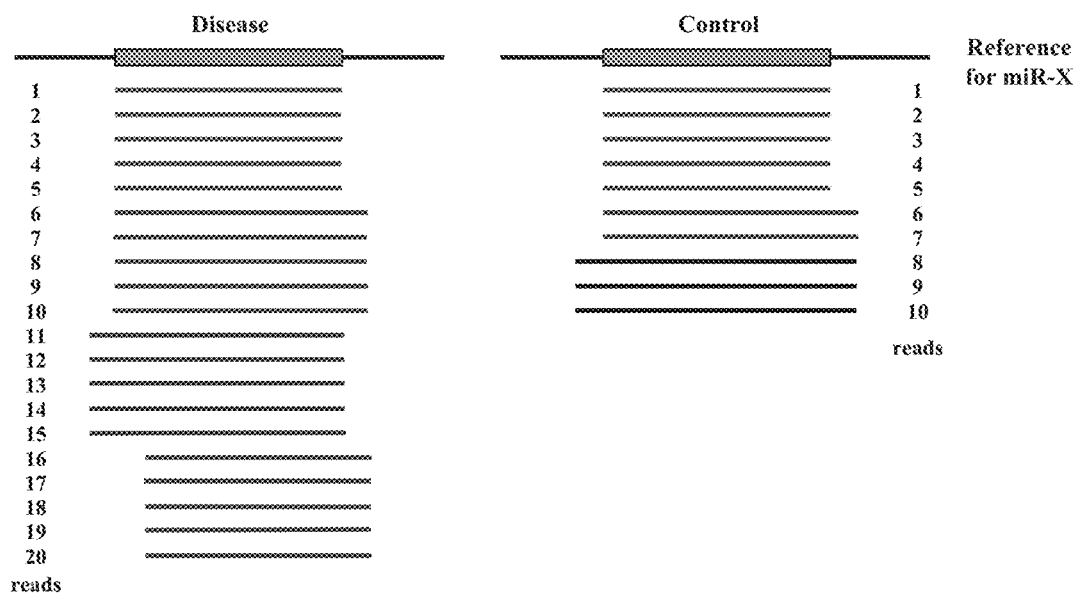
FIGS. 3A and 3B illustrate how miRNA sequencing data is sorted and quantified across samples according to embodiments of the present invention.

In various aspects and embodiments, the invention provides a method for identifying or detecting binary small RNA (sRNA) predictors of a disease or a condition. The method comprises identifying one or more sRNA sequences that are present in one or more samples of an experimental cohort, and which are not present in any of the samples in a comparator cohort ("positive sRNA predictors"). In some embodiments, the method further comprises identifying one or more sRNA sequences that are present in one or more samples of the comparator cohort, and which are not present in any of the samples of the experimental cohort ("negative sRNA predictors"). In contrast to identifying dysregulated sRNAs (such as miRNAs that are up- or down-regulated), the invention identifies sRNAs that are binary predictors, that is, sRNAs that are only present in one cohort (e.g., an experimental cohort) and not another (e.g., a comparator cohort). Further, by quantifying reads for individual sequences (e.g., iso-miRs), without consolidating reads to annotated reference sequences, the invention unlocks the diagnostic utility of miRs and other sRNAs.

In some embodiments, the presence of the one or more sRNA predictors (positive and/or negative predictors) is tested in an independent cohort of experimental and comparator samples, to evaluate the ability of the sRNA predictors to discriminate samples, thereby validating the diagnostic, prognostic, or other utility of the sRNA predictors. Diagnostic kits that detect one or a panel of sRNA predictors (positive and/or negative predictors) in a sample can be prepared in any desired detection format, including quantitative or qualitative PCR or hybridization-based assays, as described more fully herein.

In various embodiments, sRNA sequencing data is generated or provided from a sample or group of samples across an experimental cohort and comparator cohort, and sRNA predictors are identified in the RNA sequencing data according to the following disclosure.

sRNA sequencing enriches and sequences small RNA species, such as microRNA (miRNA), Piwi-interacting RNA (piRNA), small interfering RNA (siRNA), vault RNA (vtRNA), small nucleolar RNA (snoRNA), transfer RNA-derived small RNAs (tsRNA), ribosomal RNA-derived small RNA fragments (rsRNA), small rRNA-derived RNA (srRNA), and small nuclear RNA (U-RNA). For example, in providing the sRNA sequencing data, input material may be enriched for small RNAs. Sequence library construction is performed with sRNA-enriched material using any of several processes or commercially-available kits depending on the high-throughput sequencing platform being employed. Generally, sRNA sequencing library preparation comprises isolating total RNA from samples, size fractionation, ligation of sequencing adaptors, reverse transcription and PCR amplification, and DNA sequencing.

More particularly, in a given sample all the RNA (i.e. total RNA) is extracted and isolated. The small RNAs are isolated by size fractionation, for example, by running the isolated RNA on a denaturing polyacrylamide gel (or using any of a variety of commercially available kits). A ligation step then adds adaptors to both ends of the small RNAs, which act as primer binding sites during reverse transcription and PCR amplification. For example, a preadenylated single strand DNA 3'-adaptor followed by a 5'-adaptor are ligated to the small RNAs using a ligating enzyme such as T4 RNA Ligase 2 Truncated (T4 Rnl2tr K227Q). The adaptors are designed to capture small RNAs with a 5'-phosphate and 3'-hydroxyl group, characteristic of biologically processed small RNAs (e.g., microRNAs), rather than RNA degradation products with a 5' hydroxyl and 3' phosphate group. The sRNA library is then reverse transcribed and amplified by PCR. This step converts the small adaptor ligated RNAs into cDNA clones that are the template for the sequencing reaction. Primers designed with unique nucleotide tags can also be used in this step to create ID tags (i.e., bar codes) in pooled library multiplex sequencing.

Any DNA sequencing platform can be employed, including any next-generation sequencing platform such as pyrosequencing (e.g., 454 Life Sciences), polymerase-based sequence-by-synthesis (e.g., Illumina), or sequencing-by-ligation (e.g., ABI Solid Sequencing platform), among others.

In various embodiments, sequencing data can be generated and/or provided from historical studies, and evaluated for sRNA predictors according to the following disclosure.

The sequencing data can be in any format, such as FASTA or FASTQ format. FASTA format is a text-based format for representing nucleotide sequences, where nucleotides are represented using single-letter codes. The format also allows for sequence names and comments to precede the sequences. FASTQ format includes corresponding quality scores. Both the sequence letter and quality score are each encoded with a single ASCII character for brevity.

sRNA predictors can be identified in any biological samples, including solid tissues and/or biological fluids. sRNA predictors can be identified in prokaryotic or eukaryotic organisms, including animals (e.g., vertebrates and invertebrates), plants, microbes (e.g., bacteria and yeast), or in some embodiments, cultured cells derived from these sources. For example, in some embodiments the experimental and comparator samples are biological fluid samples from human or animal subjects (e.g., a mammalian subject), such as blood, serum, plasma, urine, saliva, or cerebrospinal fluid. miRNAs can be found in biological fluid, as a result of a secretory mechanism that may play an important role in cell-to-cell signaling. See, Kosaka N, et al., *Circulating microRNA in body fluid: a new potential biomarker for cancer diagnosis and prognosis, Cancer Sci.* 2010; 101: 2087-2092). miRs from cerebrospinal fluid and serum have been profiled according to conventional methods with the goal of stratifying patients for disease status and pathology features. Burgos K, et al., *Profiles of Extracellular miRNA in Cerebrospinal Fluid and Serum from Patients with Alzheimer's and Parkinson's Diseases Correlate with Disease Status and Features of Pathology, PLOS ONE* Vol. 9, Issue 5 (2014). Thus, samples in the experimental cohort and the comparator cohort can be biological fluid samples, such as blood, serum, plasma, urine, saliva, or cerebrospinal fluid. In some embodiments, sRNA predictors are identified in at least two different types of fluid samples. For example, with regard to detection of neurodegenerative disease, sRNA predictors can be identified in both blood (or serum) and cerebrospinal fluid.

An experimental cohort is a collection of samples that have a defined condition. The experimental cohort can be a collection of samples from human or animal subjects or patients. Conditions include, in some embodiments, neurodegenerative diseases, cardiovascular diseases, inflammatory and/or immunological diseases, and cancers, including particular conditions described more fully below. Experimental cohorts can be further defined based on late-stage or early-stage disease, or course of disease progression, treatment received, and patient response to treatment. An experimental cohort generally comprises a plurality of samples, but in various embodiments, includes at least 1 sample, or at least about 5 samples, or at least about 10 samples, or at least about 15 samples, or at least about 20 samples, or at least about 25 samples, or at least about 50 samples, or at least about 75 samples, or at least about 100 samples, or at least about 150 samples, or at least about 200 samples, or at least about 250 samples. Larger experimental cohorts (e.g., at least 100 samples) are preferred in some embodiments.

A comparator cohort is a collection of samples that do not have the condition that defines the experimental cohort. For example, the comparator cohort can include samples from subjects or patients identified as healthy comparators, or otherwise having a different condition or disease, including conditions or diseases with similar, but different symptoms to the disease or condition of interest (e.g., similar symptoms to the disease or condition that defines the experimental cohort samples). A comparator cohort generally comprises a plurality of samples, but in various embodiments, includes at least 1 sample, or at least about 5 samples, or at least about 10 samples, or at least about 15 samples, or at least about 20 samples, or at least about 25 samples, or at least about 50 samples, or at least about 75 samples, or at least about 100 samples, or at least about 150 samples, or at least about 200 samples, or at least about 250 samples. Larger comparator cohorts are preferred in some embodiments (e.g., at least 100 samples), however the comparator cohort may be similar in size to or smaller than the experimental cohort. In some embodiments, the comparator cohort is similar to the experimental cohort in patient make-up, in terms of, for example, age, gender, and/or ethnicity.

sRNA predictors can be identified for various utilities in understanding the state of cells or organisms, including utilities in human and animal health, as well as agriculture. For example, the invention finds use in diagnostics, prognostics, drug discovery, toxicology, and therapeutics including personalized medicine. In some embodiments, the invention provides for diagnosis or stratification of a human or animal disease. For example, sRNA predictors can be identified for detecting a disease state, including early stage or asymptomatic disease (e.g., before noticeable or substantial symptoms) or distinguishing diseases or conditions that manifest with similar symptoms. In other embodiments, sRNA predictors are identified that distinguish disease courses, such as slowly and quickly progressing disease states, or disease subtypes (e.g., relapsing remitting MS, secondary progressive MS, primary progressive MS, or progressive relapsing MS), or stratify for disease severity. In these embodiments, experimental and comparator cohorts are designed to distinguish two or more disease states, based upon classification of each patient's disease across the two or more states. In still other embodiments, sRNA predictors identify patients for response to one or more available therapeutic regimens. In these embodiments, experimental and comparator cohorts are designed to distinguish responses to treatment (e.g., by classifying patient samples based upon treatment received by each patient and/or the response achieved). In some embodiments, sRNA predictors are identified that distinguish a toxic response to an environmental or pharmaceutical agent.

In some embodiments, the presence and/or absence of sRNA predictors are applied as surrogate endpoints to establish safety and/or efficacy of a candidate agent, or for treatment monitoring, by evaluating the presence and/or absence of the sRNA predictors in patient samples during clinical trials or during treatment. For example, positive predictors may be found before treatment with a candidate agent, and may decrease or be eliminated with successful drug treatment. Alternatively, or in addition, negative predictors may be absent before treatment, but may emerge during successful treatment.

With respect to human or animal diagnostics, various types of diseases and conditions can be evaluated in accordance with various embodiments, including neurodegenerative disease, cardiovascular disease, inflammatory and/or immunological disease, and cancer.

Neurodegenerative disease is an umbrella term for the progressive loss of structure or function of neurons, including death of neurons. Exemplary neurodegenerative diseases include Alzheimer's Disease, Amyotrophic Lateral Sclerosis (ALS), Huntington's Disease, Multiple Sclerosis, Parkinson's Disease, and various types of dementia (e.g., Frontotemporal Dementia, Lewy Body Dementia, or Vascular Dementia). Neurodegenerative conditions generally result in progressive degeneration and/or death of neuronal cells. In some embodiments, the neurodegenerative disease results in dementia in at least a substantial portion of patients. In some embodiments, the neurodegenerative disease results in a motion disorder in at least a substantial portion of patients. While conditions can be late on-set, in some embodiments, the disease can manifest as early on-set (e.g., before about 50 years of age).

In some embodiments, sRNA predictors are identified in a cohort of Alzheimer's Disease (AD) samples. AD is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Alzheimer's Disease has been hypothesized to be a protein misfolding disease, caused by accumulation of abnormally folded Amyloid-beta and Tau proteins in the brain. In some embodiments, the experimental cohort samples are biological fluid samples from patients diagnosed as having AD. Comparator cohort samples can be patients identified as not having AD, and may optionally include patients with other (non-AD) neurodegenerative or inflammatory disease.

In some embodiments, sRNA predictors are identified in a cohort of Parkinson's Disease (PD) samples. PD manifests as bradykinesia, rigidity, resting tremor and posture instability. PD is a degenerative disorder of the central nervous system that involves the death of dopamine-generating cells in the substantia nigra, a region of the midbrain. The mechanism by which the brain cells in PD are lost may involve an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. In some embodiments, the experimental cohort samples are biological fluid samples from patients diagnosed as having PD. Comparator cohort samples can be patients identified as not having PD, and may optionally include patients with other (non-PD) neurodegenerative or inflammatory disease.

In some embodiments, sRNA predictors are identified in a cohort of Huntington's Disease (HD) samples. HD causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. Mutant Huntington is an aggregate-prone protein. In some embodiments, the experimental cohort samples are biological fluid samples from patients diagnosed as having HD. Comparator cohort samples can be patients identified as not having HD, and may optionally include patients with other (non-HD) neurodegenerative or inflammatory disease.

In some embodiments, sRNA predictors are identified in a cohort of Amyotrophic Lateral Sclerosis (ALS) samples. ALS is a disease in which motor neurons are selectively targeted for degeneration. Some patients with familial ALS have a missense mutation in the gene encoding the antioxidant enzyme Cu/Zn superoxide dismutase 1 (SOD1). TDP-43 and FUS protein aggregates have been implicated in some cases of the disease, and a mutation in chromosome 9 (C9orf72) is thought to be the most common known cause of sporadic ALS. In some embodiments, the experimental cohort samples are biological fluid samples from patients diagnosed as having ALS. Comparator cohort samples can be patients identified as not having ALS, and may optionally include patients with other (non-ALS) neurodegenerative disease.

In some embodiments, sRNA predictors are identified in a cohort of samples from migraine subjects, such as biological fluid samples from migraine subjects. In some embodiments, the migraine is episodic migraine, chronic migraine, or cluster headache. sRNA predictors in these embodiments are useful for evaluating the subject's condition, or alternatively or in addition, selecting an appropriate treatment. Comparator cohort samples can be subjects identified as not having migraine, and may optionally include patients with other non-migraine conditions, or a different form of migraine from the experimental cohort.

Cardiovascular disease (CVD) is a class of diseases that involve the heart or blood vessels. Cardiovascular disease includes coronary artery diseases (CAD) such as angina and myocardial infarction. Other CVDs are stroke, heart failure, hypertensive heart disease, rheumatic heart disease, cardiomyopathy, heart arrhythmia, congenital heart disease, valvular heart disease, carditis, aortic aneurysms, peripheral artery disease, and venous thrombosis.

The underlying mechanisms of coronary artery disease, stroke, and peripheral artery disease involve atherosclerosis, which may be caused by high blood pressure, smoking, diabetes, lack of exercise, obesity, high blood cholesterol, poor diet, and excessive alcohol consumption, among other things. It is estimated that 90% of CVD is preventable by improving risk factors through: healthy eating, exercise, avoidance of tobacco smoke, limiting alcohol intake, and treating high blood pressure, for example. In some embodiments, the experimental cohort comprises samples from patients having coronary artery disease, peripheral artery disease, cerebrovascular disease, cardiomyopathy, hypertensive heart disease, heart failure (e.g., congestive heart failure), pulmonary heart disease, cardiac dysrhythmia, inflammatory heart disease, endocarditis, myocarditis, inflammatory cardiomegaly, valvular heart disease, congenital heart disease, or rheumatic heart disease. The comparator cohort can comprise samples from patients that do not have the CVD, or a distinct CVD from the experimental cohort.

In some embodiments, sRNA predictors are identified to stratify patients for risk of an acute event related to CVD, such as myocardial infarction or stroke. Existing cardiovascular disease or a previous cardiovascular event, such as a heart attack or stroke, is the strongest predictor of a future cardiovascular event. Age, sex, smoking, blood pressure, blood lipids and diabetes are important predictors of future cardiovascular disease in people who are not known to have cardiovascular disease. These measures, and sometimes others, may be combined into composite risk scores to estimate an individual's future risk of cardiovascular disease. Numerous risk scores exist although their respective merits are debated. Other diagnostic tests and biomarkers remain under evaluation but currently these lack clear-cut evidence to support their routine use (e.g., family history, coronary artery calcification score, high sensitivity C-reactive protein (hs-CRP), ankle brachial index, lipoprotein subclasses and particle concentration, lipoprotein(a), apolipoproteins A-I and B, fibrinogen, white blood cell count, homocysteine, N-terminal pro B-type natriuretic peptide (NT-proBNP), and markers of kidney function). In some embodiments, the experimental cohort comprises patients at a high risk of myocardial infarction or stroke (e.g., top 25% or top 20% or top 10% of risk scores), and the comparator cohort comprises patients with relatively low risk scores for the same (e.g., bottom quartile or less).

In some embodiments, the sRNA predictor identifies or evaluates an immunological or inflammatory disease. For example, in some embodiments, the condition is an autoimmune or inflammatory disorder, such as Lupus (SLE), Scleroderma, Vasculitis, Diabetes mellitus (e.g., Type 1 or Type 2), Graves' disease, Rheumatoid arthritis, Multiple Sclerosis, Fibromyalgia, Psoriasis, Crohn's Disease, Celiac Disease, COPD, or a fibrotic condition such as pulmonary fibrosis (e.g., IPF). In some embodiments, the condition is an inflammatory condition, which may manifest as type I hypersensitivity, type II hypersensitivity, type III hypersensitivity, and/or type IV hypersensitivity. The inflammatory condition may be chronic. In some embodiments, the experimental cohort samples are biological fluid samples from patients diagnosed as having a particular inflammatory disease. Comparator cohort samples can be patients identified as not having the particular inflammatory disease, and may optionally include patients with other inflammatory disease. In some embodiments, the comparator cohort comprises patients with a positive or negative (or even toxic) response to a particular treatment regimen.

In some embodiments, the sRNA predictor is predictive of the presence of cancer, or the presence of an aggressive cancer, or is predictive of remission or recurrence, metastasis, progression free interval, overall survival, or response to treatment (e.g., radiation therapy, chemotherapy, or treatment with a checkpoint inhibitor selected from anti-CTLA4, PD-1, PD-L, IDO, or CAR T-cell therapy). In some embodiments, the sRNA predictor is predictive of high toxicity upon treatment with a particular agent. In some embodiments, the sRNA predictors are predictive of a complete response of a particular cancer to a particular treatment. The cancer may be Carcinoma, Sarcoma, Lymphoma, Germ cell, or Blastoma. The cancer can occur in sites including, but not limited to lung, skin, breast, ovary, intestine, pancreas, bone, and brain, among others. In some embodiments, the cancer is stage I or stage II cancer. In other embodiments, the cancer is stage Ill or stage IV.

Illustrative cancers include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome. In some embodiments, the experimental cohort samples are biological fluid samples from patient diagnosed as having a particular defined cancer. Comparator cohort samples can be patients identified as not having the cancer, and may optionally include patients with other non-cancerous disease or condition.

The sRNA predictor may be identified by a software program that quantifies the number of reads for each unique sRNA sequence in each sample in the experimental and comparator sample cohorts. In various embodiments, the software program trims the adaptor sequences from the individual sequences, so as to identify individual sRNAs, including miRs and iso-miRs and other sRNAs. In this manner, iso-miRs with templated and non-templated variations at the 3'- and 5'-end are identified.

"iso-miR" refers to those sequences that have variations with respect to the reference miRNA sequence (e.g., as used by miRBase). In miRBase, each miRNA is associated with a miRNA precursor and with one or two mature miRNA (-5p and -3p). Deep sequencing has detected a large amount of variability in miRNA biogenesis, meaning that from the same miRNA precursor many different sequences can be generated. There are four main variations of iso-miRs: (1) 5' trimming, where the 5' cleavage site is upstream or downstream from the referenced miRNA sequence; (2) 3' trimming, where the 3' cleavage site is upstream or downstream from the reference miRNA sequence; (3) 3' nucleotide addition, where nucleotides are added to the 3' end of the reference miRNA; and (4) nucleotide substitution, where nucleotides are changed from the miRNA precursor.

The software program in some embodiments trims a user-defined 3' sequencing adaptor from the sRNA sequence reads. The adaptor is defined by the user, based on the sequencing platform. By removing the adaptor sequence, iso-miRs and other sRNAs can be identified and quantified in samples. For example, in some embodiments the software program searches for regular expressions corresponding to a user-defined 3' adaptor and deletes them from the sRNA sequence reads as follows:

a. adaptor sequence
 b. adaptor sequence permitting 1 wild-card
 c. adaptor sequence permitting 1 insertion
 d. adaptor sequence permitting 1 deletion
 e. adaptor sequence permitting 2 deletions
 f. adaptor sequence permitting 1 deletion and 1 wild-card
 g. adaptor sequence permitting 1 insertion and 1 wild-card
 h. adaptor sequence permitting 2 wild-cards
 i. adaptor sequence permitting 3 wild-cards
 j. adaptor sequence permitting 4 wild cards.

A wild-card is defined as being any one of the 4 deoxyribonucleic acids: (A) adenine, (T) thymine, (G) guanine, or (C) cytosine. However, the first nucleotide at the 5' end of the user-specified 3' adaptor sequence is not altered (e.g., not considered an insertion or deletion or otherwise subject to wild-card change), thus preserving sRNA sequences at the junction where the 3' terminal nucleotide of the sRNA is ligated to the 5' terminal nucleotide of the 3' adapter. If the 5' terminal nucleotide of the user-specified 3' adaptor does not correspond with what the user has specified, the 3' adapter sequence is not trimmed, but can be independently verified, if needed.

In some embodiments, sRNA having a length of at least 15 nucleotides, or at least 20 nucleotides (after trimming), are considered for analysis.

After trimming, the sequence reads from the experimental cohort and the comparator cohort can be each compiled into a dictionary, and compared, to identify sequences that are present in samples of the experimental cohort, but not the comparator cohort (e.g. positive predictors), and/or to identify sequences that are present in the comparator cohort, but not the experimental cohort (e.g. negative predictors). Sequence reads that are in both cohorts are discarded, and sequence reads that are unique to either the experimental cohort or comparator cohort are added to an output file, the unique reads being candidate sRNA predictors. The output file annotates the unique sequences and the count of the unique sequence reads for each sample or group of samples in the cohorts. In various embodiments, the sequence reads are not filtered by a quality score. Further, sRNA sequences are not aligned to a reference sequence, and thus, each sequence can be individually quantified across samples.

In some embodiments, sRNA predictors are selected that have a count of (or an average count of) at least 5, at least 10, at least 20, at least 50, at least 75, at least 100, at least 200, at least 500, or at least 1000 reads in samples that are positive for the predictor (e.g., in the experimental cohort for positive predictors or the comparator cohort for negative predictors). In some embodiments, one or more (or all) positive sRNA predictors are present in at least about 5%, or at least about 100 of the experimental cohort samples, or at least about 15% of experimental cohort samples, or at least about 20% of experimental cohort samples, or at least about 30% of experimental cohort samples, or at least about 40% or at least about 50% of experimental cohort samples. In some embodiments, at least 1, or at least about 5, or at least about 10, or at least about 20, or at least about 30, or at least about 40, or at least about 50, or at least about 100 positive sRNA predictors are identified in the experimental cohort, and a plurality of which (e.g., from 1 to 100 or from 1 to 50, or from 1 to 10) may be selected for inclusion in an sRNA predictor panel. In some embodiments, from 4 to 100, or from 10 to 100, or from 20 to 100 positive sRNA predictors are selected for inclusion in a panel.

In some embodiments, the negative sRNA predictors are present in at least about 5% of the comparator cohort samples, or at least 10/o of the comparator cohort samples, or at least about 15% of the comparator cohort samples, or at least about 20% of comparator cohort samples, or at least about 300/% of comparator cohort samples, or at least about 40% or at least about 50% of comparator cohort samples. In some embodiments, at least 1, or at least about 5, or at least about 10, or at least about 20, or at least about 30, or at least about 40, or at least about 50, or at least about 100 negative sRNA predictors are identified in the comparator cohort, and a plurality of which (e.g., from 1 to 100, or from 1 to 50, or from 1 to 10) may be selected for inclusion in an sRNA predictor panel. In some embodiments, from 4 to 100, or from 10 to 100, or from 20 to 100 negative sRNA predictors are selected for inclusion in a panel.

A panel of sRNA predictors is selected for validation or detection of the condition in independent samples. For example, a panel of from 2 to about 100 sRNA predictors can be selected, where the presence of any one positive predictor, and the absence of all of the negative predictors is predictive of the condition that defines the experimental cohort. In some embodiments, the presence of any 2, 3, 4, 5, 6, 7, 8, 9 or 10 positive sRNA predictors is predictive of the condition, optionally with the absence of the negative predictors. In some embodiments, a panel of from 2 to about 40 sRNA predictors are selected, or from 2 to about 30, or from 2 to about 20, or from 2 to about 10 sRNA predictors are selected for inclusion in a panel. In some embodiments, from 4 to about 100, or from 4 to about 50, or from 4 to about 20, or from 4 to about 15, or from 4 to about 10 sRNA predictors are selected for inclusion in the panel. In these embodiments, the panel may optionally comprise at least 5, or at least 10, or at least 20 sRNA predictors. While not each experimental sample will be positive for each positive predictor, the panel is large enough to provide at least about 75%, at least about 80%, at least about 85%, at least about 90%, at least about 95%, or about 100% coverage for the condition in the experimental cohort or in independent samples. That is, the presence of from 1 to 10 positive sRNA predictors (e.g., any one or two) in a sample may be predictive of the condition that defines the experimental cohort. The sample may further be negative for the panel of negative predictors (e.g., from 1 to 10 or from 1 to 5 negative predictors). Validation samples can be evaluated by sRNA sequencing, or alternatively by RT-PCR or other assay.

In various embodiments, detection of the sRNA predictors is migrated to one of various detection platforms (e.g., other than RNA sequencing), which can employ reverse-transcription, amplification, and/or hybridization of a probe, including quantitative or qualitative PCR, or RealTime PCR. PCR detection formats can employ stem-loop primers for RT-PCR in some embodiments, and optionally in connection with fluorescently-labeled probes.

Generally, a real-time polymerase chain reaction (qPCR) monitors the amplification of a targeted DNA molecule during the PCR, i.e. in real-time. Real-time PCR can be used quantitatively, and semi-quantitatively. Two common methods for the detection of PCR products in real-time PCR are: (1) non-specific fluorescent dyes that intercalate with any double-stranded DNA (e.g., SYBR Green (I or II)), and (2) sequence-specific DNA probes consisting of oligonucleotides that are labelled with a fluorescent reporter which permits detection only after hybridization of the probe with its complementary sequence (e.g. TAQMAN).

In some embodiments, the assay format is TAQMAN real-time PCR. TAQMAN probes are hydrolysis probes that are designed to increase the specificity of quantitative PCR. The TAQMAN probe principle relies on the 5' to 3' exonuclease activity of Taq polymerase to cleave a dual-labeled probe during hybridization to the complementary target sequence, with fluorophore-based detection. TAQMAN probes are dual labeled with a fluorophore and a quencher, and when the fluorophore is cleaved from the oligonucleotide probe by the Taq exonuclease activity, the fluorophore signal is detected (e.g., the signal is no longer quenched by the proximity of the labels). As in other quantitative PCR methods, the resulting fluorescence signal permits quantitative measurements of the accumulation of the product during the exponential stages of the PCR. The TAQMAN probe format provides high sensitivity and specificity of the detection.

In some embodiments, sRNA predictors present in the sample are converted to cDNA using specific primers, e.g., a stem-loop primer. Amplification of the cDNA may then be quantified in real time, for example, by detecting the signal from a fluorescent reporting molecule, where the signal intensity correlates with the level of DNA at each amplification cycle.

Alternatively, sRNA predictors in the panel, or their amplicons, are detected by hybridization. Exemplary platforms include surface plasmon resonance (SPR) and microarray technology. Detection platforms can use microfluidics in some embodiments, for convenient sample processing and sRNA detection.

Generally, any method for determining the presence of sRNAs in samples can be employed. Such methods further include nucleic acid sequence based amplification (NASBA), flap endonuclease-based assays, as well as direct RNA capture with branched DNA (QuantiGene™), Hybrid Capture™ (Digene), or nCounter™ miRNA detection (nanostring). The assay format, in addition to determining the presence of miRNAs and other sRNAs may also provide for the control of, inter alia, intrinsic signal intensity variation. Such controls may include, for example, controls for background signal intensity and/or sample processing, and/or hybridization efficiency, as well as other desirable controls for detecting sRNAs in patient samples (e.g., collectively referred to as "normalization controls").

In some embodiments, the assay format is a flap endonuclease-based format, such as the Invader™ assay (Third Wave Technologies). In the case of using the invader method, an invader probe containing a sequence specific to the region 3' to a target site, and a primary probe containing a sequence specific to the region 5' to the target site of a template and an unrelated flap sequence, are prepared. Cleavase is then allowed to act in the presence of these probes, the target molecule, as well as a FRET probe containing a sequence complementary to the flap sequence and an auto-complementary sequence that is labeled with both a fluorescent dye and a quencher. When the primary probe hybridizes with the template, the 3' end of the invader probe penetrates the target site, and this structure is cleaved by the Cleavase resulting in dissociation of the flap. The flap binds to the FRET probe and the fluorescent dye portion is cleaved by the Cleavase resulting in emission of fluorescence.

In some embodiments, RNA is extracted from the sample prior to sRNA processing for detection. RNA may be purified using a variety of standard procedures as described, for example, in RNA Methodologies, *A laboratory guide for isolation and characterization,* 2nd edition, 1998, Robert E. Farrell, Jr., Ed., Academic Press. In addition, there are various processes as well as products commercially available for isolation of small molecular weight RNAs, including mirVANA™ Paris miRNA Isolation Kit (Ambion), miRNeasy™ kits (Qiagen), MagMAX™ kits (Life Technologies), and Pure Link™ kits (Life Technologies). For example, small molecular weight RNAs may be isolated by organic extraction followed by purification on a glass fiber filter. Alternative methods for isolating miRNAs include hybridization to magnetic beads. Alternatively, miRNA processing for detection (e.g., cDNA synthesis) may be conducted in the biofluid sample, that is, without an RNA extraction step.

Generally, assays can be constructed such that each assay is at least 80%, or at least 85%, or at least 90%, or at least 95%, or at least 98% specific for the sRNA (e.g., iso-miR) over an annotated sequence and/or other non-predictive iso-miRs. Annotated sequences can be determined with reference to miRBase. For example, in preparing sRNA predictor-specific real-time PCR assays, PCR primers and fluorescent probes can be prepared and tested for their level of specificity. Bicyclic nucleotides (e.g., LNA, cET, and MOE) or other nucleotide modifications (including base modifications) can be employed in probes to increase the sensitivity or specificity of detection.

In some embodiments, the invention provides a kit comprising a panel of from 2 to about 100 sRNA predictor assays, or from about 2 to about 75 sRNA predictor assay, or from 2 to about 40 sRNA predictor assays, or from 2 to about 30, or from 2 to about 20, or from 2 to about 10 sRNA predictor assays. In these embodiments, the kit may comprise at least 5, at least 10, at least 20 sRNA predictor assays (e.g., reagents for such assays). For example, the kit may comprise at least one positive predictor and at least one negative predictor. In various embodiments, the kit comprises at least 5 positive predictors and at least 2 negative predictors. In some embodiments, the kit comprises a panel of from 4 to about 20, or from 4 to about 15, or from 4 to about 10 sRNA predictor assays. Such assays may comprise reverse transcription (RT) primers, amplification primers and probes (such as fluorescent probes or dual labeled probes) specific for the sRNA predictors over annotated sequences as well as other (non-predictive) 5'- and/or 3'-templated and/or non-templated variations. In some embodiments, the kit is in the form of an array or other substrate containing probes for detection of sRNA predictors by hybridization.

In other aspects, the invention provides a method for determining a condition of a cell or organism (including with respect to animals, plants, and microbes). In some embodiments, the invention provides a method for evaluating the condition of an subject or patient. In some embodiments, the method comprises obtaining a biological sample (such as a biological fluid sample from a subject or patient), and identifying the presence or absence of one or more sRNA predictors (identified according to the method described above), thereby determining the condition of the cell or organism (e.g., the condition of the patient). For example, the condition identified is the condition that defines the experimental cohort, with respect to the comparator cohort. In some embodiments, the sRNA predictor(s) are identified in a subject or patient sample by a detection technology that involves amplification and/or probe hybridization, such as RT-PCR or TAQMAN assays, or other detection formats.

In various embodiments, the sample is a biological fluid sample from a patient, and is selected from blood, serum, plasma, urine, saliva, or cerebrospinal fluid. For example, the sample may be a blood sample or samples derived therefrom. In some embodiments, at least two biological samples are tested, which may be selected from blood, serum, plasma, urine, saliva, and cerebrospinal fluid.

In various embodiments, the patient is suspected of having a neurodegenerative disease, a cardiovascular disease, an inflammatory and/or immunological disease, or a cancer. For example, the patient may be displaying one or more symptoms thereof.

In some embodiments, the patient is suspected of having a neurodegenerative disease selected from Amyotrophic Lateral Sclerosis (ALS), Parkinson's Disease (PD), Alzheimer's Disease (AD), Huntington's Disease (HD), or Multiple Sclerosis (MS). In some embodiments, the patient has signs of dementia or a movement disorder, or CNS lesions.

In some embodiments, the patient has or is suspected of having or is at risk of a cardiovascular disease (CVD) optionally selected from coronary artery disease (CAD) such as angina and myocardial infarction, stroke, congestive heart failure, hypertensive heart disease, rheumatic heart disease, cardiomyopathy, heart arrhythmia, congenital heart disease, valvular heart disease, carditis, aortic aneurysms, peripheral artery disease, and venous thrombosis. In some embodiments, the patient has a high risk score for heart attack or stroke.

In some embodiments, the patient displays symptoms of an immune or inflammatory disorder, such as Lupus (SLE), Scleroderma, Vasculitis, Diabetes mellitus (e.g., Type 1 or Type 2), Graves' Disease, Rheumatoid Arthritis, Multiple Sclerosis, Fibromyalgia, Psoriasis, Crohn's Disease, Celiac Disease, COPD, or pulmonary fibrosis (e.g., IPF). In some embodiments, the condition is an inflammatory condition, which may manifest as type I hypersensitivity, type II hypersensitivity, type III hypersensitivity, and/or type IV hypersensitivity.

In some embodiments, the patient has cancer, is suspected of having cancer, or is being screened for cancer. The cancer may be bowel cancer, lung cancer, skin cancer, ovarian cancer, breast cancer among others. In some embodiments, the cancer is stage I or stage II cancer. In other embodiments, the cancer is stage III or stage IV. In some embodiments, the patient is a candidate for treatment with a checkpoint inhibitor or CAR-T therapy, chemotherapy, neoadjuvant therapy, or radiation therapy.

Illustrative cancers include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

In some embodiments, the sample is tested for the presence or absence of at least about 2, or at least about 5, or at least about 10, or at least about 20, or at least about 30, or at least about 40, or at least about 50 sRNA predictors (e.g., from 4 to 50 sRNA predictors), where the presence of from 1 to about 10 positive predictors (or from 1 to 5 sRNA positive predictors) is indicative of the condition. Optionally, the absence of from 1 to 10 negative predictors is further indicative of the condition. In some embodiments, the presence of positive predictors in the panel, and the absence of negative predictors in the panel is scored to determine a probability that the patient has the condition of interest.

Patients that test positive for the condition of interest, can then be further diagnosed and/or treated accordingly for the defined condition.

In other aspects of the invention, positive and/or negative predictors can be employed to classify a mixed population of cells in vivo or ex vivo, through targeted expression of a gene with a detectable or biological impact. For example, a desired protein can be expressed from a gene construct (using a vector such as a plasmid or viral vector) or expressed from mRNA delivered to cells in vivo or ex vivo. In these embodiments, the gene is delivered under the regulatory control of target site(s) for the one or more small RNA predictors. The target site(s) (target sites for hybridization with the predictors) can be placed in non-coding segments, such as the 3' and/or 5' UTRs, such that the encoded protein is only expressed in biologically significant amounts when the desired predictor(s) are absent in the cell. The protein encoded by the construct may be a reporter protein, a transcriptional activator, a transcriptional repressor, a pro-apoptotic protein, a pro-survival protein, a lytic protein, an enzyme, a cytokine, a toxin, or a cell-surface receptor.

For example, the encoded protein can be a fluorescent protein or an enzyme capable of performing a detectable reaction (e.g., β-galactosidase, alkaline phosphatase, luciferase, or horseradish peroxidase). In these embodiments, all cells expressing the positive or negative predictor will be differentiated from other cells, allowing a sub-population of cells to be accurately identified ex vivo or in vivo. In some embodiments, the genetic constructs enable the identification of specific cell populations for isolation, such as a desired immune cell type or cells with a desired stem cell phenotype, e.g., by fluorescent cell sorting. In vivo, such detectable constructs can also be useful in treatment of cancer, by, for example, aiding in precise surgical removal of the cancer or targeted radiation or chemotherapy.

In some embodiments, the encoded protein can modulate a cellular pathway or activity of the cell. For example, the alteration in cellular activity can cause or alter apoptotic cell death, replication (e.g., DNA or cellular replication), cell differentiation, or cell migration. For example, apoptosis can be the result of the expression of a death receptor (e.g., FasR or TNFR), death receptor ligand (e.g., FasL or TNF), a caspase (e.g., caspase 3 or caspase 9), cytochrome-c, a BH3-containing proapoptotic protein (e.g., BAX, BAD, BID, or BIM), apoptosis inducing factor (AIF), or a protein toxin. Alternatively, growth arrest can be the result of expression of a protein such as p21, p19ARF, p53, or RB protein, or tumor suppressor protein. In some embodiments, the encoded protein is a growth factor or cytokine, either an inflammatory or anti-inflammatory cytokine.

In some embodiments, the genetic construct (whether DNA or RNA) is administered to a subject having cancer, an immunological disorder such as an autoimmune diseases, a neurodegenerative disorder, a cardiovascular disorder, a metabolic disorder, or an infection (bacterial, viral, or parasitic infection). Administration of the genetic construct targets individual cells with precision based on internal molecular cues (presence or absence of one or more predictors).

In some embodiments, the construct contains a target site specific for a negative sRNA predictor to avoid expression of the encoded protein in non-diseased cells (where the negative predictor will be present). In some embodiments, the encoded protein induces cell death or apoptosis in cells that do not express the negative predictor. In some embodiments, the protein is a toxin or protein that induces apoptosis or cell death.

In other embodiments, the construct contains a target site specific for a positive sRNA predictor to avoid expression of the encoded protein in diseased cells. For example, the encoded protein may protect the cells from insult (e.g., a pro-survival protein), such as an insult in the form of chemotherapy, radiation, or immuno-oncology. In these embodiments, the encoded protein may be under the regulatory control of a target site for a small RNA predictor only present in diseased cells (positive predictor). In these embodiments, the construct would be expressed and limit damage and toxicity in non-diseased cells.

Other aspects and embodiments of the invention will be apparent from the following examples.

EXAMPLES

The conventional approach to miRNA sequence analysis for diagnostic use involves identifying up- or down-regulated miRNAs, typically with reference to an annotated sequence. For data processing and analysis, the goal is to identify dysregulated miRNAs (up or down-regulated) for validation in larger cohorts using targeted assays such as TAQMAN-based qPCR.

For example, a small RNA fraction is extracted/isolated from samples, 3' and 5' adapters are ligated to sRNAs, and sRNAs are reverse transcribed, amplified, and sequenced. During processing, adapter sequences are trimmed (typically using a Smith-Waterman Algorithm or close derivative thereof), and reads are aligned to a reference sequence. Residual sequences are sometimes analyzed by predictive programs to identify new miRNAs. Read numbers are quantified for each reference miRNA. See FIG. 1A illustrating the conventional approach. Current data analysis methods analyze fold-changes between samples (FIG. 1B). Typically, deltas are around 1.8 to 5-fold, which is insufficient for a meaningful diagnostic test.

Figure 3B:
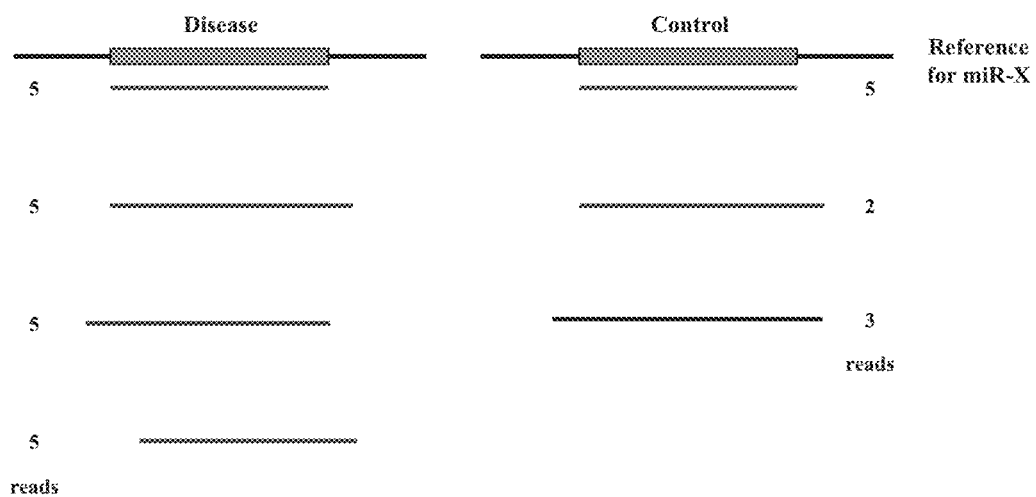
Figure 4:
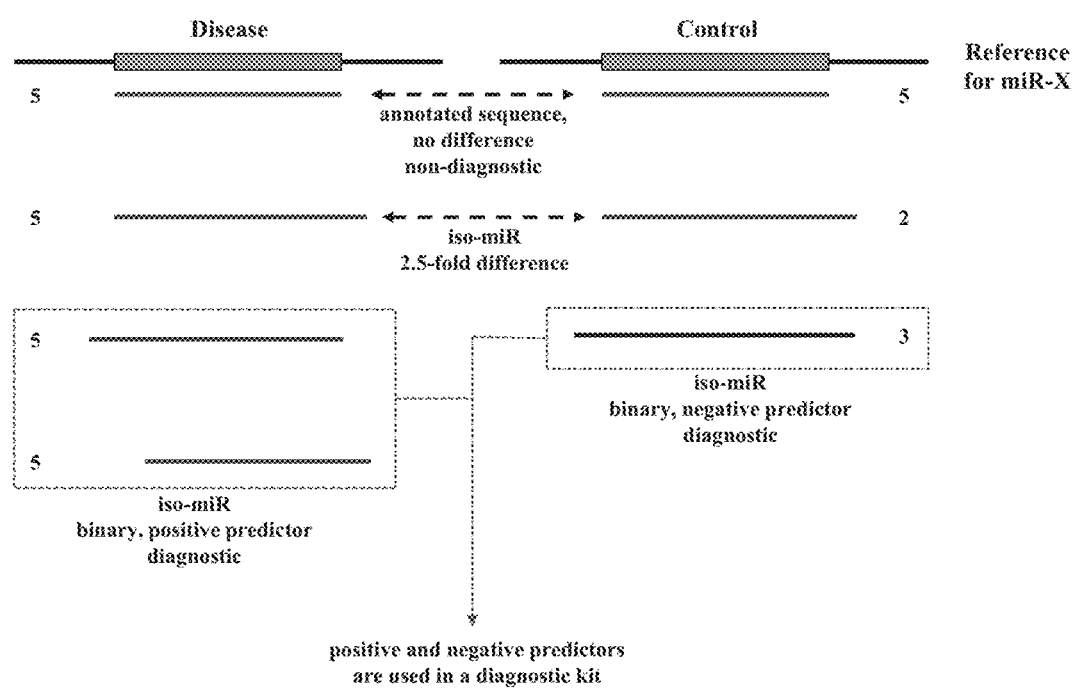
FIG. 4 illustrates the analytic method described herein for identifying positive and negative predictors in small RNA sequencing data. As depicted for miR-X, there are 2 binary, positive predictors for in the Disease sample and 1 binary, negative predictor in the Control sample. These positive and negative predictors can be used in a diagnostic panel to test for the condition in which they have been identified. Furthermore.

Furthermore, the term miRNA is a misnomer. For any given miRNA there are multiple iso-miRs that harbor templated and/or non-templated nucleotides at the 5'- and/or 3'-end (see FIG. 2 and FIG. 3). The conventional method for analyzing miRNA sequence data 'masks' iso-miR data, since trimmed sequence reads are aligned back to a reference list of miRNA sequences (e.g. a comprehensive list of all cloned miRNAs, from whatever species the research is being performed in), typically sourced from miRBase, a miRNA sequence depository). Further, TAQMAN assays used in down-stream validation are highly-specific for the sequences they are designed to detected, and they are designed against the same reference list of miRNAs from miRBase. Thus, these TAQMAN assays only detect annotated miRNAs, and not closely related sequence variants of the annotated miRNA, including iso-miRs. See, Chen C, et al., *Real-time quantification of microRNAs by stem-loop RT-PCR*, Nucleic Acids Res. 2005, 33(20) e179. Also, see FIG. 5 showing specificity of TAQMAN assays against closely related variants.

In embodiments of the process described herein, raw sequencing data is trimmed by identifying and removing the 3' adapter sequences. The 3' adapter sequence to be trimmed is user-specified, and thus RNA sequencing data generated from any RNA-sequence platform can be used. For example, the software can employ 'pattern matching' to identify regular expressions (i.e. the user-specified 3' adapter), and if desired a defined level of variation to the user-specified 3' adapter, and then deletes them. In this approach there is no 'fuzzy trimming', as is seen with a Smith-Waterman Algorithm, because here only regular expressions, and if desired, the level of user-specified variation to the regular expression, is trimmed. Further differentiation from a Smith-Waterman Algorithm, the 5' most nucleotide (i.e. the nucleotide that defines the junction between the small RNA and the 3' adapter) must be present in a read in order for the regular expression to be recognized by the software program and trimmed. Embodiments of the software accommodate up to: 5 wild cards, 1 insertion, 2 deletions, 1 insertion+1 wild card, and 1 deletion+1 wild card. The program can trim nearly 100% of the sequence data, whereas most programs only trim around 80 to 85%. Trimmed sequence data is not aligned to a reference, thereby retaining the individual iso-miR data, as well as many other small RNA families that would otherwise be eliminated, such as: miRNAs not listed in the reference, Piwi-interacting RNA (piRNA), small interfering RNA (siRNA), vault RNA (vtRNA), small nucleolar RNA (snoRNA), transfer RNA-derived small RNA (tsRNA), ribosomal RNA-derived small RNA fragments (rsRNA), small rDNA-derived RNA (srRNA), and small nuclear RNA (U-RNA).

Data is sorted based on individual sequence reads, and each sequence read is condensed to a single line and quantified. Using the condensed/quantified data, the process uses a program to look for 'unique' or 'binary' RNA sequences that are only present in the cohort of interest. For example, to identify positive predictors, the sequence read content of Group B (i.e. the comparator cohort) is compiled into a dictionary, and the sequence read content of each sample in Group A (i.e. the experimental cohort) is compared against the dictionary and the following equation is executed: Group A–Group B. Positive predictors (i.e. unique/binary reads) found in cohort A are output to a new file and quantified. To identify negative predictors, the sequence read content of Group A (i.e. the experimental cohort) is compiled into a dictionary, and the sequence read content of each sample in Group B (i.e. the comparator cohort) is compared against the dictionary and the following equation is executed: Group B−Group A. Negative predictors (i.e. unique/binary reads) found in cohort B are output to a new file and quantified. When identifying positive predictors and negative predictors, sequences found in both B and A are discarded. That is, the only data that conventional methods use, is discarded in accordance with embodiments of the present disclosure. If positive and/or negative predictors are present in >1 sample, data for each sample may be compiled in the same output file, and total read count across all the samples is calculated. Read frequency (% of samples with which a particular binary sequence occurred) is also calculated. Since the sequences being identified are 100% unique to a particular Group or Cohort, they are 'perfect predictors'.

Once binary predictors are identified, stem-loop-RT based TAQMAN qPCR assays may be designed against any of the sequences of interest. Stem-loop-RT based TAQMAN qPCR assays are ultra-specific and give single nucleotide resolution (FIG. 5). Where assays do not give 100% specificity, introduction of chemical modifications into the stem-loop-RT primer and/or qPCR primers, and/or TAQMAN probe can increase the base-pairing specificity and/or increase the melting temperature (Tm) of annealing. Stem-loop-RT-based TAQMAN qPCR assays can detect as few as 7 copies of a small RNA in a sample.

Example 1: Huntington's Disease

Small RNA sequencing data from GSE64977 was obtained from the GEO Database. Hoss A G, et al., *miR-10b-5p expression in Huntington's disease brain relates to age of onset and the extent of striatal involvement. BMC Med Genomics,* 2015, Mar. 1; 8:10.

Sequence Read Archive (.sra) files were converted to .fastq format using the SRA Toolkit v2.8.0. 1). Raw small RNA sequencing data was trimmed using the methods described with the following adapter sequence: TGGAAT-TCTCGGGTGCCAAGGAACTC (SEQ ID NO:1). Resulting biomarkers had to be equal to or greater than twenty nucleotides after trimming to be considered for downstream analysis.

Positive and negative predictors were identified by comparing (28) Huntington's Disease samples to (36) healthy control samples. Biomarkers had to be equal to or greater than twenty nucleotides, and had to occur at a frequency of equal to or greater than 10% of the population to be considered.

Figure 6:
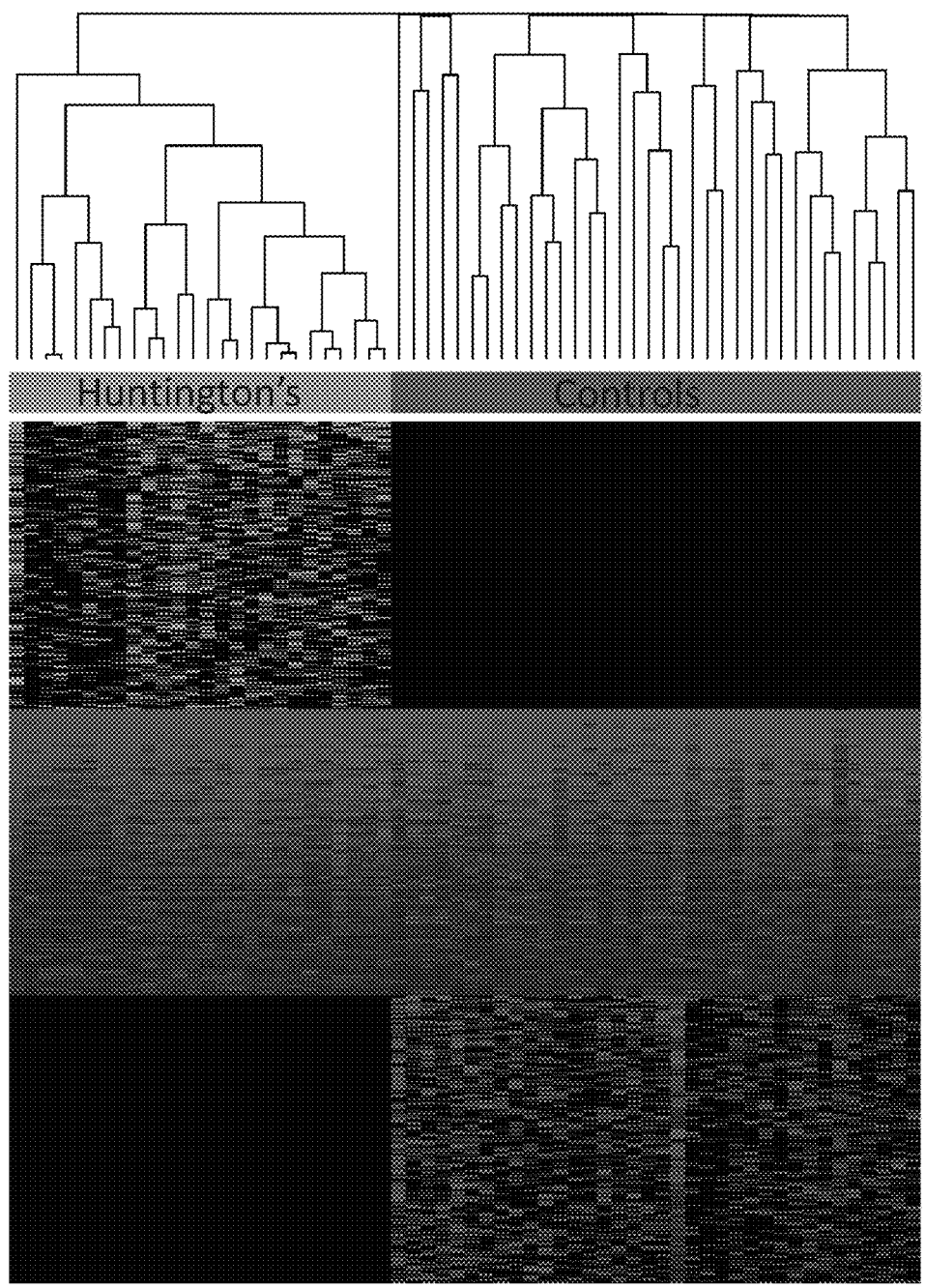
FIG. 6 is a heat map in which the top 335 highest frequency small RNAs found in Huntington's Disease (top), healthy controls (bottom), and both Huntington's Disease and healthy controls (middle) were clustered using Ward's agglomerative clustering with incomplete linkage.

The top 335 highest frequency small RNAs found in Huntington's Disease, healthy controls, and both Huntington's Disease and healthy controls were clustered using Ward's agglomerative clustering with incomplete linkage (FIG. 6).

Eight positive small RNA predictors (only found in Huntington's Disease patients) were selected for experimental validation. Reverse transcription (RT) hairpin-based TaqMan quantitative polymerase chain reaction (qPCR) assays (ThermoFisher Scientific) were designed to specifically target those small RNAs.

Total RNA was extracted from the frontal cortex (region BA9) of 32 healthy control and 32 Huntington's Disease patients that were postmortem verified for pathology and disease-grade, using the miRNeasy Purification Kit from Qiagen (Catalog Number: 217004). cDNA libraries were multiplex-reverse transcribed from 1000 ng of total RNA using the TaqMan MicroRNA Reverse Transcription Kit (ThermoFisher Scientific, Catalog Number: 4366596) and pooled RT primers, according to the manufacturer's protocol. Resultant cDNA libraries were diluted 1:500 with 10 mM Tris pH 8.0 (Millipore, Catalog Number: 648314).

Small RNA predictors were analyzed from 2 ul of cDNA in triplicate, by TaqMan qPCR using targeted primers and probes, and Universal Master Mix II (ThermoFisher Scientific, Catalog Number: 4440043), in a 5 ul reaction, thermocycled 50-times, in an ABI 7900HT Fast Real-Time PCR System fitted with a 384-well heat block.

The following acceptance criteria was applied step-wise to the raw Cycle Threshold (Ct) values:

(1) Ct values over 39.999999 were excluded from analysis, (2) samples must have a minimum of 2 duplicates to be considered for analysis, (3) the coefficient of variance (% CV) must be less than 5%; 1 triplicate was allowed to be masked to meet the % CV acceptance criteria (samples with only 2 duplicates could not be masked).

Figure 7:
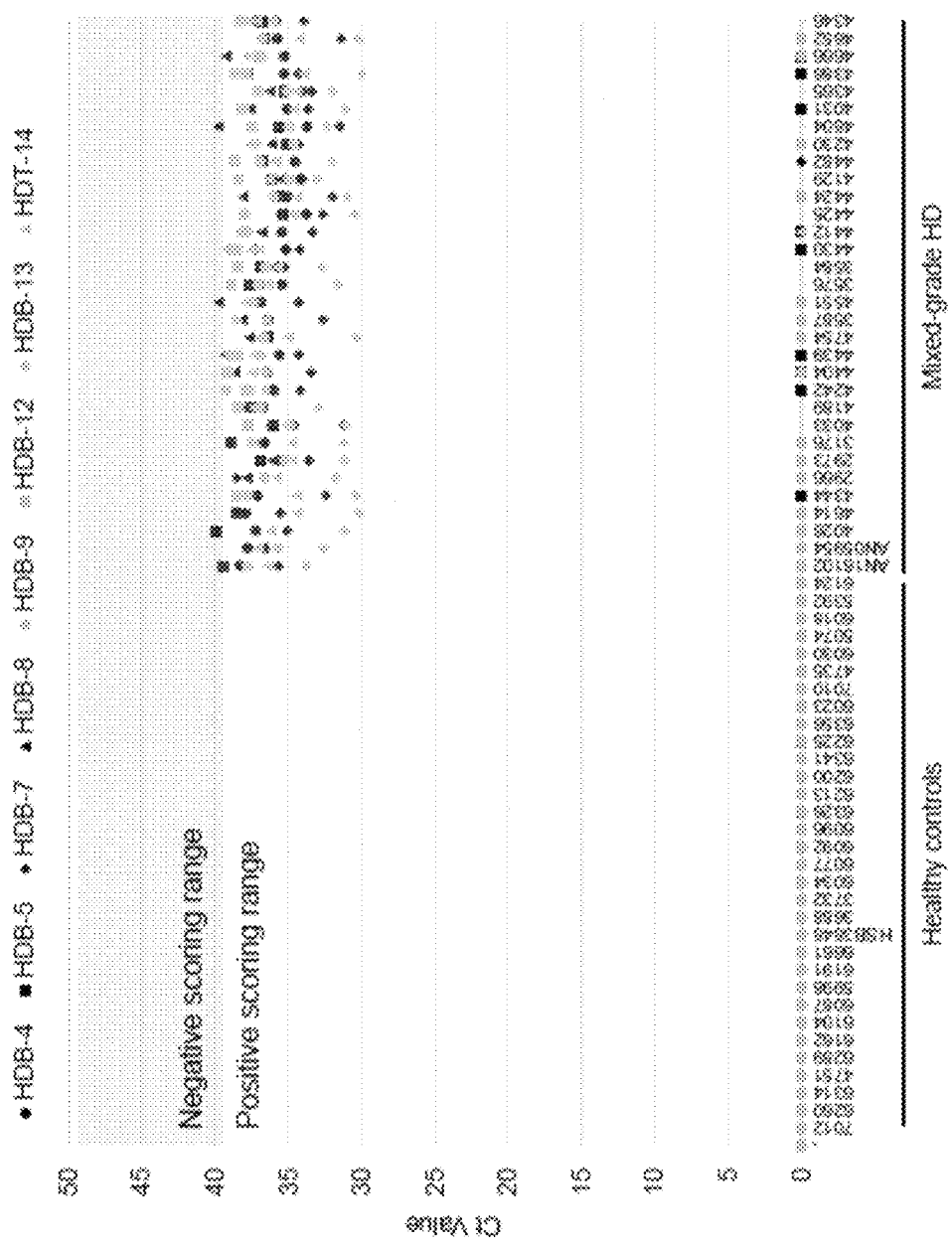
FIG. 7 shows experimental validation of eight positive small RNA predictors identified in Huntington's Disease samples, using Reverse transcription (RT) hairpin-based TAQMAN quantitative polymerase chain reaction (qPCR) assays (ThermoFisher Scientific). Clinical information (disease vs non-disease, and disease grade) was unmasked and the samples were decoded and Ct values were plotted for healthy controls and Huntington's Disease.
Figure 8:
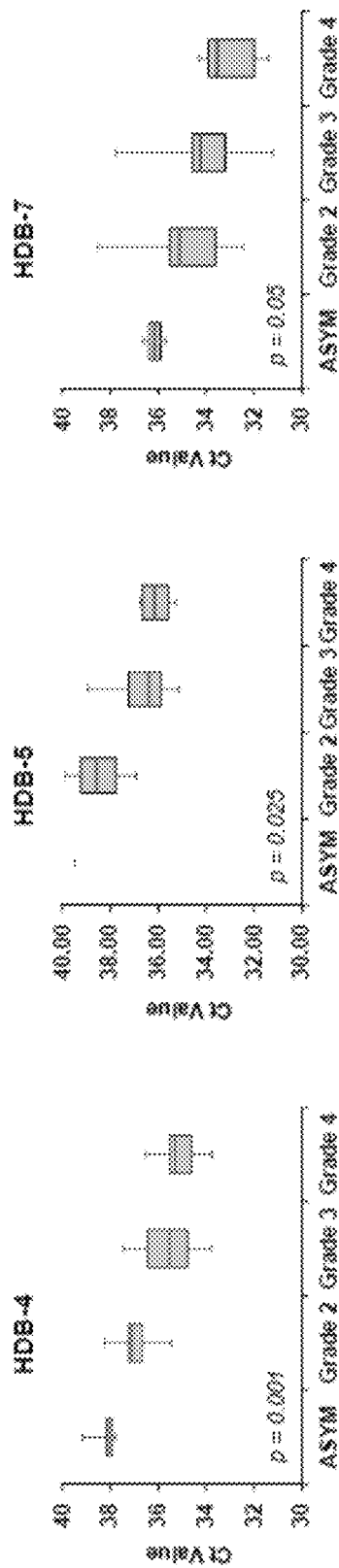
FIG. 8 shows an analysis of eight biomarkers for a correlation of Ct to disease grade using Box-Whisker plots. Ct values of three biomarkers named Huntington's Disease Biomarker-4 (HDB-4), HDB-5, HDB-7 correlated with disease grade by Analysis of Variance (ANOVA).

Clinical information (disease vs non-disease, and disease grade) was unmasked and the samples were decoded and Ct values were plotted for healthy controls and Huntington's Disease (FIG. 7). Eight biomarkers were analyzed for a correlation of Ct to disease grade using Box-Whisker plots. Ct values of three biomarkers named Huntington's Disease Biomarker-4 (HDB-4), HDB-5, HDB-7 correlated with disease grade by Analysis of Variance (ANOVA) (FIG. 8).

Example 2: Parkinson's Disease

Small RNA sequencing data from GSE72962 and GSE64977 was obtained from the GEO Database. Hoss A G, et al., microRNA Profiles in Parkinson's Disease Prefrontal Cortex, Front Aging Neurosci. 2016, Mar. 1; 8:36.

Small RNA sequencing data from phs000727.v1.p1 was obtained from the dbGAP Database. Sequence Read Archive (.sra) files were converted to .fastq format using the SRA Toolkit v2.8.0. Raw small RNA sequencing data was trimmed using the methods described with the following adapter sequence: TGGAATTCTCGGGTGC-CAAGGAACTC (SEQ ID NO:1). Resulting biomarkers had to be equal to or greater than twenty nucleotides after trimming to be considered for downstream analysis.

To identify positive and negative binary predictors in frontal cortex (region BA9), 29 Parkinson's samples were compared to 36 healthy control samples. Biomarkers had to be equal to or greater than twenty nucleotides, and had to occur at a frequency of equal to or greater than 10% of the population to be considered.

To identify positive and negative binary predictors in cerebrospinal fluid, 66 Parkinson's samples and 68 healthy controls were compared. Biomarkers had to be equal to or greater than twenty nucleotides, and had to occur at a frequency of equal to or greater than 10% of the population to be considered.

To identify positive and negative binary predictors in serum, 60 Parkinson's samples and 70 healthy controls were compared. Biomarkers had to be equal to or greater than twenty nucleotides, and had to occur at a frequency of equal to or greater than 10% of the population to be considered.

Figure 9:
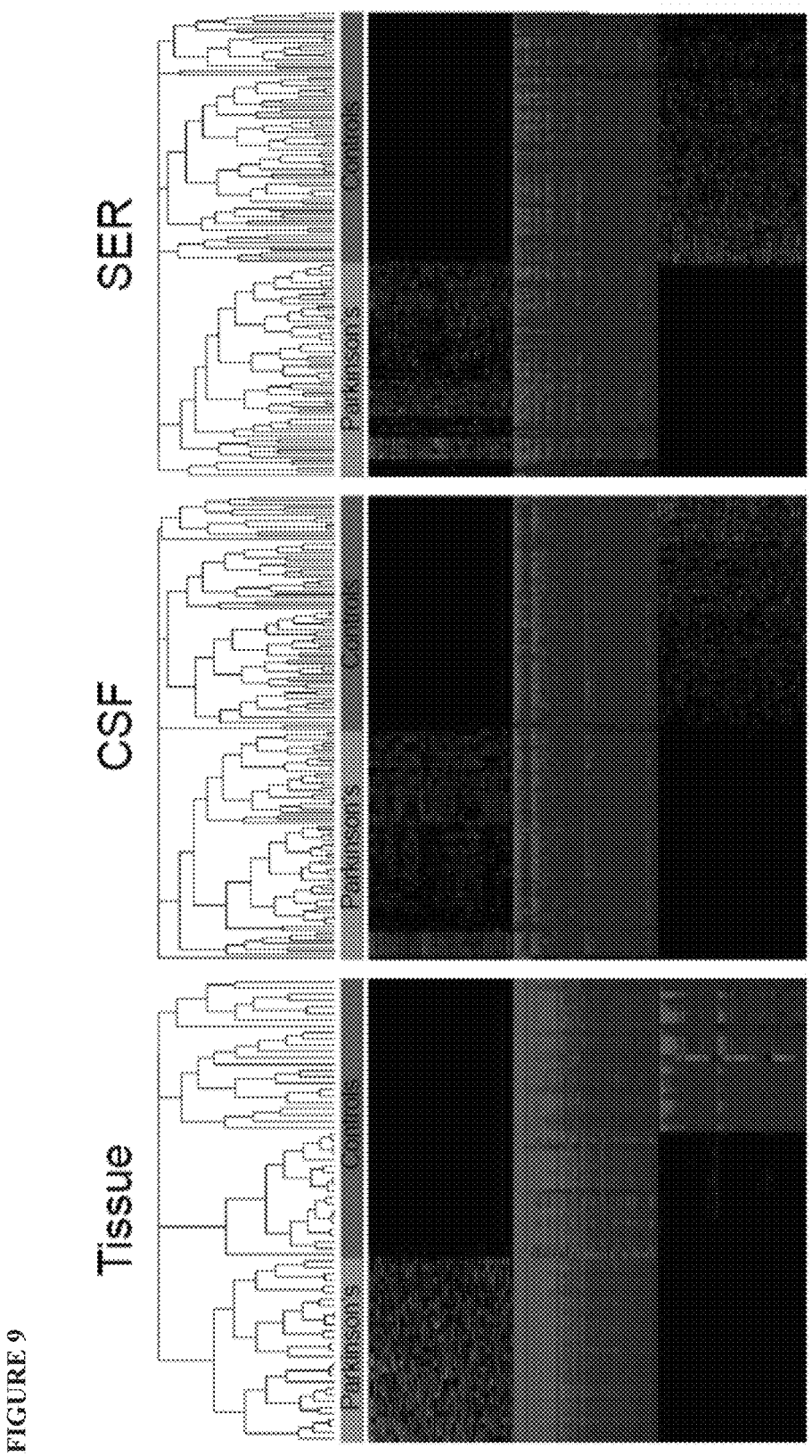
FIG. 9 is a heat map in which the top 335 highest frequency small RNAs found in Parkinson's Disease (top), healthy controls (bottom), and both Parkinson's Disease and healthy controls (middle) were clustered using Ward's agglomerative clustering with incomplete linkage. Analysis of tissue from frontal cortex (region BA9), CSF (cerebrospinal fluid), and Serum is shown.
Figure 10:
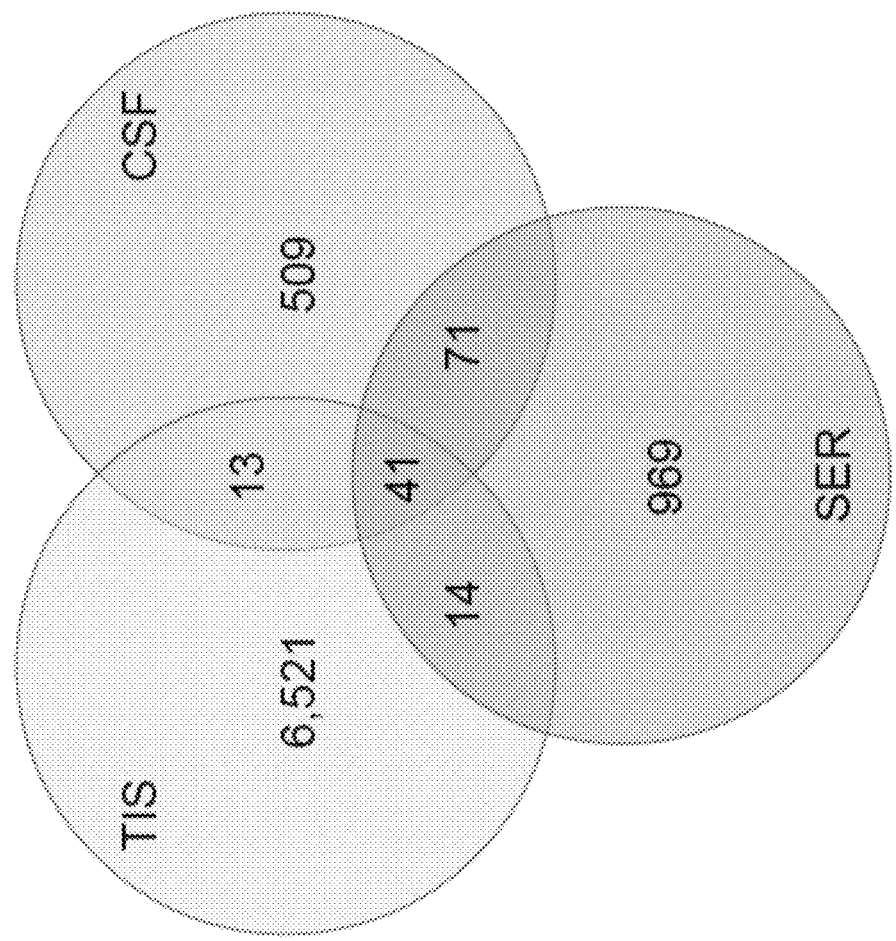
FIG. 10 illustrates tissue-specific biomarker overlap for Parkinson's disease predictors. (TIS indicates tissue, CSF indicates cerebrospinal fluid, SER indicates serum).

The top 335 highest frequency small RNAs found in Parkinson's Disease, healthy controls, and both Parkinson's Disease and healthy controls were clustered using Ward's agglomerative clustering with incomplete linkage (FIG. 9). Tissue-specific biomarker overlap was determined; only biomarkers having a frequency of greater than 10% were considered for analysis (FIG. 10). As shown in FIG. 10, sRNA predictors can be found in multiple tissues and biological fluids including serum, and thus can be developed as convenient markers for neurodegenerative diseases such as PD.

Example 3: Alzheimer's Disease

Small RNA sequencing data from GSE46579 was obtained from the GEO Database. Burgos K, et al., *Profiles of extracellular miRNA in cerebrospinal fluid and serum from patients with Alzheimer's and Parkinson's diseases correlate with disease status and features of pathology,* 2014 May 5; 9(5):e94839; Leidinger P, et al., *A blood based 12-miRNA signature of Alzheimer disease patients PLoS One* (2014); *Genome Biol.* 2013 Jul. 29; 14(7):R78.

Small RNA sequencing data from phs000727.v1.p1 was obtained from the dbGAP Database. Sequence Read Archive (.sra) files were converted to .fastq format using the SRA Toolkit v2.8.0. Raw small RNA sequencing data was trimmed using the methods described with the following adapter sequence: TGGAATTCTCGGGTGC-CAAGGAACTC (SEQ ID NO:1). Resulting biomarkers had to be equal to or greater than twenty nucleotides after trimming to be considered for downstream analysis.

To identify positive and negative binary predictors in cerebrospinal fluid, 67 Alzheimer's samples were compared to 68 healthy controls. Biomarkers had to be equal to or greater than twenty nucleotides, and had to occur at a frequency of equal to or greater than 10% of the population to be considered.

To identify positive and negative binary predictors in serum, 62 Alzheimer's samples were compared to 70 healthy controls. Biomarkers had to be equal to or greater than twenty nucleotides, and had to occur at a frequency of equal to or greater than 10% of the population to be considered.

To identify positive and negative binary predictors in PAXgene (whole blood), 48 Alzheimer's samples were compared to 22 healthy control samples. Biomarkers had to be equal to or greater than twenty nucleotides, and had to occur at a frequency of equal to or greater than 10% of the population to be considered.

Figure 11:
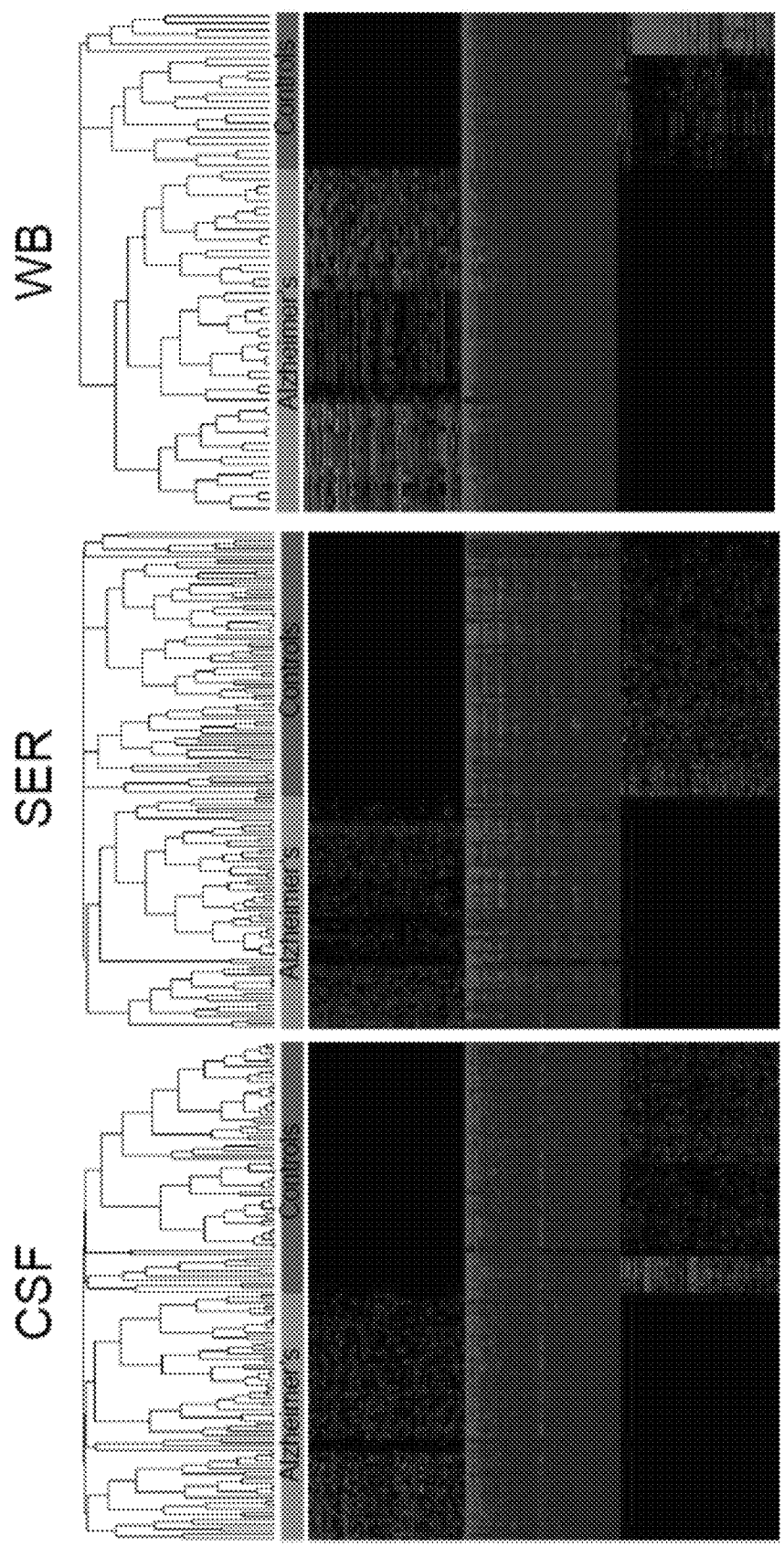
FIG. 11 is a heat map in which the top 335 highest frequency small RNAs found in Alzheimer's Disease (top), healthy controls (bottom), and both Alzheimer's Disease and healthy controls (middle) were clustered using Ward's agglomerative clustering with incomplete linkage. Analysis of CSF, Serum, and Whole Blood (WB) is shown.
Figure 12:
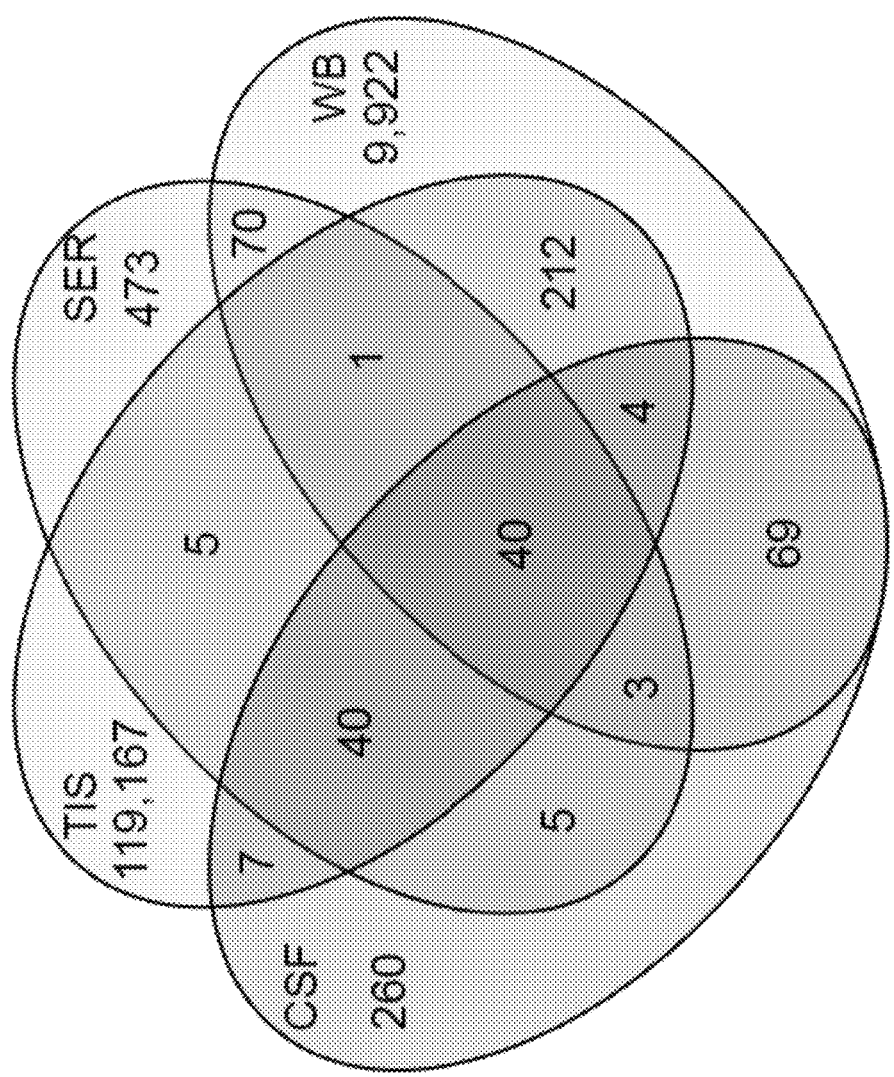
FIG. 12 illustrates tissue-specific biomarker overlap for Alzheimer's Disease (TIS indicates tissue, CSF indicates cerebrospinal fluid, SER indicates serum, WB indicates whole blood).

The top 335 highest frequency small RNAs found in Alzheimer's Disease, healthy controls, and both Alzheimer's Disease and healthy controls were clustered using Ward's agglomerative clustering with incomplete linkage (FIG. 11). Tissue-specific biomarker overlap was determined; only biomarkers having a frequency of greater than 10% were considered for analysis (FIG. 12). As shown in FIG. 12, predictors are found in multiple tissues and biological fluids.

Example 4: Breast Cancer

Small RNA sequencing data from GSE29173 was obtained from the GEO Database. Farazi T A, et al., *MicroRNA sequence and expression analysis in breast tumors by deep sequencing, Cancer Res.* 2011 Jul. 1; 71(13): 4443-53.

Sequence Read Archive (.sra) files were converted to .fastq format using the SRA Toolkit v2.8.0. Raw small RNA sequencing data was trimmed using the methods described with the following adapter sequence: TGGAAT-TCTCGGGTGCCAAGGAACTC (SEQ ID NO:1), followed by subsequent trimming of a 5-mer barcode on each sequence read. Resulting biomarkers had to be equal to or greater than twenty nucleotides after trimming to be considered for downstream analysis.

Figure 13:
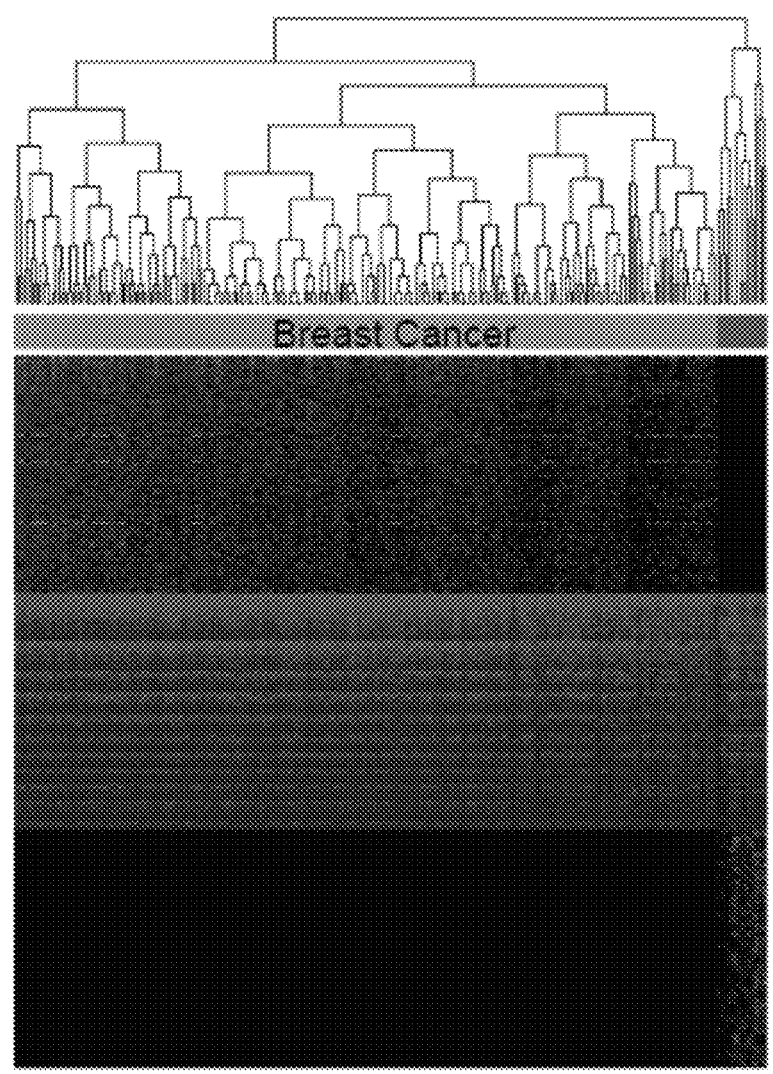
FIG. 13 is a heat map in which the top 335 highest frequency small RNAs found in breast cancer tissue (top), healthy controls (bottom), and both breast cancer and healthy controls (middle) were clustered using Ward's agglomerative clustering with incomplete linkage.

To identify positive and negative binary predictors in breast cancer tissue, 229 breast cancer samples were compared to 16 healthy controls. Biomarkers had to be equal to or greater than twenty nucleotides, and had to occur at a frequency of equal to or greater than 10% of the population to be considered. The top 335 highest frequency small RNAs found in breast cancer, healthy controls, and both breast cancer and healthy controls were clustered using Ward's agglomerative clustering with incomplete linkage (FIG. 13).

The invention claimed is:

1. A method for identifying small RNA (sRNA) predictors for neurodegenerative disease, comprising:

(1) providing sRNA sequencing data from an experimental cohort and a comparator cohort of solid tissue or biological fluid samples, the sRNA sequencing data being generated by a sequencing-by-synthesis sequencing platform;

wherein the samples of the experimental cohort and the samples of the comparator cohort are from patients having the presence or absence, respectively, of a neurodegenerative disease;

wherein the sRNA sequencing data comprises sequence reads having adaptor sequences at 5'- and 3'-ends, and sRNA sequences are defined from the sequence reads by deletion of the adaptor sequences so as to identify variations at the 3'- and 5'-ends of the sRNA sequences, the sRNA sequences being defined without consolidating sequence reads to a reference sequence;

(2) selecting sRNA sequences that are present in at least 10% of the samples in the experimental cohort and which are not present in any samples of the comparator cohort, thereby identifying positive sRNA predictors, and wherein at least one selected sRNA sequence is an isomiR; and (3) detecting the presence and absence of the selected positive sRNA predictors in RNA extracted from samples of a validation cohort using a quantitative or qualitative PCR assay that is specific for the sRNA predictors, wherein the PCR assay employs a stem loop primer and a fluorescently-labeled probe; thereby identifying sRNA predictors for the neurodegenerative disease.

2. The method of claim 1, wherein the biological samples are biological fluid samples selected from blood, serum, plasma, urine, saliva, or cerebrospinal fluid.

3. The method of claim 1, wherein the experimental cohort and the comparator cohort each have at least 50 samples.

4. The method of claim 3, wherein the experimental cohort and the comparator cohort each have at least 100 samples.

5. The method of claim 1, wherein the neurodegenerative disease is selected from Alzheimer's Disease, Parkinson's Disease, Huntington's Disease.

6. The method of claim 1, wherein sRNA sequences are selected that have a sequence read count of at least 20 in the majority of samples that are positive for the sRNA sequence.

7. The method of claim 6, wherein sRNA sequences are selected that have a sequence read count of at least 50 in the majority of samples that are positive for the sRNA sequence.

8. The method of claim 1, wherein at least one sRNA sequence is selected that is present in at least 20% of samples in the experimental cohort.

9. The method of claim 8, wherein from 2 to 50 sRNA sequences are selected and validated using the quantitative or qualitative PCR assay.

10. The method of claim 9, wherein from 4 to 15 sRNA sequences are selected and validated using the quantitative or qualitative PCR assay.

11. The method of claim 9, wherein the quantitative or qualitative PCR assay is real time PCR.

12. The method of claim 1, wherein the isomiR has a non-templated variation at the 3'-end and/or 5' end.

13. The method of claim 1, wherein the isomiR has a templated variation at the 3' end and/or 5' end.

14. The method of claim 1, wherein about 100% of the sequence reads have adaptor sequences deleted so as to identify variations at the 3'- and 5'-ends of the sRNA sequences.

15. The method of claim 1, wherein at least one of the selected sRNA sequences is present in at least 30% of samples in the experimental cohort.

16. A method for evaluating a subject for a neurodegenerative disease, comprising: providing a biological sample from the subject, and identifying the presence or absence of the sRNA predictors identified according to the method of claim 1, wherein the sRNA predictors are detected using a PCR assay employing a stem loop primer and a fluorescently-labeled probe, wherein the presence of one or more sRNA predictors in the sample is indicative of the presence of the neurodegenerative disease, and wherein one or more of the sRNA predictors are isomiRs.

17. The method of claim 16, wherein the neurodegenerative disease Huntington's Disease.

18. The method of claim 16, wherein the neurodegenerative disease is Alzheimer's Disease.

19. The method of claim 16, wherein the neurodegenerative disease is Parkinson's Disease.

20. The method of claim 16, wherein the biological sample is blood, serum, plasma, or cerebrospinal fluid.

21. The method of claim 20, wherein the biological fluid is cerebrospinal fluid.

22. The method of claim 16, wherein presence or absence of at least five sRNA predictors are tested in the sample.

* * * * *

SEQUENCE LISTING

<160> NUMBER OF SEQ ID NOS: 14

<210> SEQ ID NO 1
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 1
tggaattctc gggtgccaag gaactc                                        26

<210> SEQ ID NO 2
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 2
atataccctg tagaaccgaa tttgtgtgg                                     29

<210> SEQ ID NO 3

```
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 3
taccctgtag aaccgaattt gtg                                              23

<210> SEQ ID NO 4
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 4
taccctgtag aaccgaattt gtga                                             24

<210> SEQ ID NO 5
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 5
accctgtaga accgaatttg tg                                               22

<210> SEQ ID NO 6
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 6
accctgtaga accgaatttg tgt                                              23

<210> SEQ ID NO 7
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 7
accctgtaga accgaatttg tga                                              23

<210> SEQ ID NO 8
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 8
taccctgtag aaccgaattt gtgg                                             24

<210> SEQ ID NO 9
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 9
```

```
accctgtaga accgaatttg tgg                                                23

<210> SEQ ID NO 10
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 10
taccctgtag aaccgaattt gtgaa                                              25

<210> SEQ ID NO 11
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 11
accctgtaga accgaatttg tgaa                                               24

<210> SEQ ID NO 12
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 12
ugagaacuga auuccauggg uu                                                 22

<210> SEQ ID NO 13
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 13
ugagaacuga auuccauggg uuu                                                23

<210> SEQ ID NO 14
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 14
ugagaacuga auuccauggg uug                                                23
```